US010087454B2

(12) United States Patent
Bilyeu et al.

(10) Patent No.: US 10,087,454 B2
(45) Date of Patent: *Oct. 2, 2018

(54) METHOD TO DEVELOP HIGH OLEIC ACID SOYBEANS USING CONVENTIONAL SOYBEAN BREEDING TECHNIQUES

(71) Applicants: The Curators of the University of Missouri, Columbia, MO (US); The United States of America, as Represented by the Secretary of Agriculture, Washington, DC (US)

(72) Inventors: Kristin D. Bilyeu, Columbia, MO (US); James Grover Shannon, Kennett, MO (US); Jeong-Dong Lee, Daegu (KR); Anh Tung Pham, Columbia, MO (US)

(73) Assignees: THE CURATORS OF THE UNIVERSITY OF MISSOURI, Columbia, MO (US); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 219 days.

This patent is subject to a terminal disclaimer.

(21) Appl. No.: 14/929,951

(22) Filed: Nov. 2, 2015

(65) Prior Publication Data
US 2016/0068853 A1    Mar. 10, 2016

Related U.S. Application Data

(62) Division of application No. 13/351,757, filed on Jan. 17, 2012, now Pat. No. 9,198,365.

(60) Provisional application No. 61/433,120, filed on Jan. 14, 2011.

(51) Int. Cl.
*C12N 15/82* (2006.01)
*A01H 1/00* (2006.01)
*A01H 5/10* (2018.01)

(52) U.S. Cl.
CPC .......... *C12N 15/8247* (2013.01); *A01H 1/00* (2013.01); *A01H 5/10* (2013.01)

(58) Field of Classification Search
None
See application file for complete search history.

(56) References Cited

U.S. PATENT DOCUMENTS

| | | | |
|---|---|---|---|
| 7,326,547 B2 | 2/2008 | Anai et al. | |
| 7,531,718 B2 | 5/2009 | Fillatti | |
| 9,198,365 B2 * | 12/2015 | Bilyeu | C12N 15/8247 |
| 2004/0034888 A1 | 2/2004 | Liu et al. | |
| 2004/0103450 A1 | 5/2004 | Anai et al. | |
| 2005/0262589 A1 | 11/2005 | Fillatti | |
| 2007/0214516 A1 | 9/2007 | Fillatti et al. | |
| 2009/0068658 A1 | 3/2009 | Anai et al. | |
| 2011/0010791 A1 | 1/2011 | Bilyeu et al. | |
| 2012/0102587 A1 | 4/2012 | Anai | |
| 2012/0192306 A1 | 7/2012 | Bilyeu et al. | |

FOREIGN PATENT DOCUMENTS

| | | | |
|---|---|---|---|
| CA | 2645148 A1 | 9/2007 | |
| CA | 2767545 A1 | 1/2011 | |
| CN | 103002727 A | 3/2013 | |
| WO | 2003/080802 A2 | 10/2003 | |
| WO | 2010/150901 A1 | 12/2010 | |
| WO | 2011/005998 A1 | 1/2011 | |

OTHER PUBLICATIONS

Alt J L et al: "Phenotypic and Molecular 1-18 Analysis of Oleate Content in the Mutant Soybean Line M23, Soybean Line M23", Crop Science: A Journal Serving the International Community of Crop Scientists, Crop Society of America, US, vol. 45, No. 5, Sep. 1, 2005, pp. 1997-2000.
Bachlava Eleni et al: "Mapping genes encoding microsomal omega-6 desaturase enzymes and their cosegregalion with QTL affecting oleate content in soybean", Crop Science, vol. 48, No. 2, Mar. 2008 (Mar. 2008), pp. 640-650.
Buhr T et al: "Ribozyme termination of RNA transcripts down-regulate seed fatty acid genes in transgenic soybean", The Plant Journal, Blackwell Scientific Publications, Oxford, GB, vol. 30, No. 2, Jan. 1, 2002 (Jan. 1, 2002), pp. 155-163.
Dewey, et al, "Molecular Analysis of Soybean Germplasm Possessing Unique Seed Oil Phenotypes", Sep. 30, 2009, downloaded from the Internet, Aug. 30, 2010 at: www.reels.usda.gov/web/crisprojectpagesI216079.html; 3 pages.
Dierking, et al., "New sources of soybean seed meal and oil composition traits identified through TILLING", BMC Plant Biology, Jul. 14, 2009, vol. 9, pp. 89-99.
European Search Report and Written Opinion in related application No. EP 10797869, dated Oct. 16, 2012, 8 pages.
GenBank Reference Sequence NP_001238342 (2014).
Hill et al, "Evaluation of the USDA Soybean Germplasm Collection: Maturity Groups VI-VII", USDA Technical Bulletin No. 1894, Jul. 2001.
Hohe et al., "A Tool for Understanding Homologous Recombination in Plants", Plant Cell Reports, Aug. 2003, pp. 1135-1142, vol. 21 No. 12.
Hoshino et al., "Novel GmFAD2-1b Mutant Alleles Created by Reverse Genetics Induce Marked Elevation of Oleic Acid Content in Soybean Seeds in Combination with GmFAD2-1a Mutant Alleles", Breeding Science, 2010, pp. 419-425, vol. 60.

(Continued)

*Primary Examiner* — Elizabeth F McElwain
(74) *Attorney, Agent, or Firm* — Thompson Coburn LLP; J. Wendy Davis

(57) ABSTRACT

The present invention is directed to a soybean plant with mutations in FAD2-1A and FAD2-1B. Moreover, the present invention is directed to seeds from said plants with altered ratios of monosaturated and polyunsaturated fats. In particular, the present invention is directed to plants where the plants exhibit elevated levels of oleic acid.

22 Claims, 6 Drawing Sheets

Specification includes a Sequence Listing.

(56) References Cited

OTHER PUBLICATIONS

Kinney, "Development of Genetically Engineered Soybean Oils for Food Applications", Journal of Food Lipids, 3: p. 273-292, 1996.

Mansur et al, "Determining the linage of quantitative trait loci to RFLP markers using extreme phenotypes of recombinant inbreds of soybean", Theoretical and Applied Genetics, 86:914-918, 1993.

McCabe, et al., "Stable Transformation of Soybean (Glycine Max) by Particle Acceleration", Bio/Technology vol. 6, Aug. 1988, pp. 923-926.

McCallum et al., "Targeting Induced Local Lesions in Genomes (TILLING) for Plant Functional Genomics", Plant Physiol. vol. 123, p. 439-442, 2000.

Monteros, "Mapping and Confirmation of Soybean Quantitative Trait Loci for Oleic Acid Content and Reaction to Asian Soybean Rust", Dissertation, University of Georgia, p. 1-173, 2006.

Oliva, et al., "Stability of Fatty Acid Profile in Soybean Genotypes with Modified See Oil Composition", Crop Science, 46:2069-2075, Sep. 2006.

PCT/US2012/021535 International Search Report & Written Opinion dated May 2, 2012, 7 pages.

PCTUS1041415 Search Report and Written Opinion dated Sep. 20, 2010, 10 pages.

Peregrine et al., Evaluation of the USDA Soybean Germplasm Collection: Maturity Groups V and Maturity Groups VI-VIII, USDA Technical Bulletin No. 1920, Apr. 2008.

Pham Anh-Tung et al: "Mutant alleles of FAD2-1A and FAD2-1B combine to produce soybeans with the high oleic acid seed oil trait", BMC Plant Biology, Biomed Central, London, GB, vol. 10, No. 1, Sep. 9, 2010, p. 195.

Sandhu, D. et al., "Enhanced Oleic Acid Content in the Soybean Mutant M23 is Associated with the Deletion in the Fad2-Ia Gene Encoding a Fatty Acid Desaturase", J. Amer. Oil Chem. Soc. (2007) 84: 229-235.

Shannon, et al., "Registration of 'Jake' Soybean, J. of Plant Registrations", vol. 1, May-Jun. 2007, 3 pages.

Takagi, Y., et al., "Inheritance of high oleic acid content in the seed oil of soybean mutant M23", Theoretical Applied Genetics 92, 179-182 (1996).

Tang, et al., "Oleate desaturase enzymes of soybean: evidence of regulation through differential stability and phosphorylation", The Plant Journal, Nov. 2005, vol. 44, No. 3, pp. 433-446.

\* cited by examiner

SEQUENCE LISTING

```
<160> NUMBER OF SEQ ID NOS: 21

<210> SEQ ID NO 1
<211> LENGTH: 1164
<212> TYPE: DNA
<213> ORGANISM: Glycine max
<220> FEATURE:
<221> NAME/KEY: CDS
<222> LOCATION: (1)..(1164)
<223> OTHER INFORMATION: nucleotide sequence of FAD2-1B mutant PI 283327
<220> FEATURE:
```

```
<221> NAME/KEY: mutation
<222> LOCATION: (66)..(66)
<223> OTHER INFORMATION: G to A mutation (silent mutation)
<220> FEATURE:
<221> NAME/KEY: mutation
<222> LOCATION: (257)..(257)
<223> OTHER INFORMATION: C to T mutation resulting in an amino acid
      substitution of Serine to Phenylalanine at amino acid 86
<220> FEATURE:
<221> NAME/KEY: mutation
<222> LOCATION: (376)..(376)
<223> OTHER INFORMATION: A to G mutation resulting in an amino acid
      substitution of Methionine to Valine at amino acid 126
<220> FEATURE:
<221> NAME/KEY: mutation
<222> LOCATION: (410)..(410)
<223> OTHER INFORMATION: C to G mutation leading to a corresponding
      amino acid mutation from Proline to Arginine at amino acid 137
<220> FEATURE:
<221> NAME/KEY: mutation
<222> LOCATION: (657)..(657)
<223> OTHER INFORMATION: C to T mutation (silent mutation)
<220> FEATURE:
<221> NAME/KEY: mutation
<222> LOCATION: (669)..(669)
<223> OTHER INFORMATION: T to C mutation (silent mutation)
<220> FEATURE:
<221> NAME/KEY: mutation
<222> LOCATION: (682)..(682)
<223> OTHER INFORMATION: T to C mutation (silent mutation)
<220> FEATURE:
<221> NAME/KEY: mutation
<222> LOCATION: (918)..(918)
<223> OTHER INFORMATION: A to G mutation (silent mutation)

<400> SEQUENCE: 1 atg ggt cta gca aag gaa aca ata atg gga ggt gga ggc cgt gtg gcc      48
Met Gly Leu Ala Lys Glu Thr Ile Met Gly Gly Gly Gly Arg Val Ala
1               5                  10                  15 aaa gtt gaa att cag caa aag aag cct ctc tca agg gtt cca aac aca      96
Lys Val Glu Ile Gln Gln Lys Lys Pro Leu Ser Arg Val Pro Asn Thr
            20                  25                  30 aag cca cca ttc act gtt ggc caa ctc aag aaa gcc att cca ccg cac     144
Lys Pro Pro Phe Thr Val Gly Gln Leu Lys Lys Ala Ile Pro Pro His
        35                  40                  45 tgc ttt cag cgt tcc ctc ctc act tca ttg tcc tat gtt gtt tat gac     192
Cys Phe Gln Arg Ser Leu Leu Thr Ser Leu Ser Tyr Val Val Tyr Asp
50                  55                  60 ctt tca ttg gct ttc att ttc tac att gcc acc acc tac ttc cac ctc     240
Leu Ser Leu Ala Phe Ile Phe Tyr Ile Ala Thr Thr Tyr Phe His Leu
65                  70                  75                  80 ctc cct cac ccc ttt ttc ctc att gca tgg cca atc tat tgg gtt ctc     288
Leu Pro His Pro Phe Phe Leu Ile Ala Trp Pro Ile Tyr Trp Val Leu
                85                  90                  95 caa ggt tgc att ctt act ggc gtg tgg gtg att gct cac gag tgt ggt     336
Gln Gly Cys Ile Leu Thr Gly Val Trp Val Ile Ala His Glu Cys Gly
            100                 105                 110 cac cat gcc ttc agc aag tac cca tgg gtt gat gat gtt gtg ggt ttg     384
His His Ala Phe Ser Lys Tyr Pro Trp Val Asp Asp Val Val Gly Leu
        115                 120                 125 acc gtt cac tca gca ctt tta gtc cgt tat ttc tca tgg aaa ata agc     432
Thr Val His Ser Ala Leu Leu Val Arg Tyr Phe Ser Trp Lys Ile Ser
    130                 135                 140 cat cgc cgc cac cac tcc aac acg ggt tcc ctt gac cgt gat gaa gtg     480
His Arg Arg His His Ser Asn Thr Gly Ser Leu Asp Arg Asp Glu Val
145                 150                 155                 160 ttt gtc cca aaa cca aaa tcc aaa gtt gca tgg tac acc aag tac ctg     528
Phe Val Pro Lys Pro Lys Ser Lys Val Ala Trp Tyr Thr Lys Tyr Leu
```

```
aac aac cct cta gga agg gct gct tct ctt ctc atc aca ctc aca ata    576
Asn Asn Pro Leu Gly Arg Ala Ala Ser Leu Leu Ile Thr Leu Thr Ile
            180                 185                 190 ggg tgg cct ttg tat tta gcc ttc aat gtc tct ggc aga ccc tat gat    624
Gly Trp Pro Leu Tyr Leu Ala Phe Asn Val Ser Gly Arg Pro Tyr Asp
        195                 200                 205 ggt ttt gct agc cac tac cac cct tat gct cct ata tat tca aac cgt    672
Gly Phe Ala Ser His Tyr His Pro Tyr Ala Pro Ile Tyr Ser Asn Arg
    210                 215                 220 gag agg ctt ctg atc tat gtc tct gat gtt gct ttg ttt tct gtg act    720
Glu Arg Leu Leu Ile Tyr Val Ser Asp Val Ala Leu Phe Ser Val Thr
225                 230                 235                 240 tac ttg ctc tac cgt gtt gca act atg aaa ggg ttg gtt tgg ctg cta    768
Tyr Leu Leu Tyr Arg Val Ala Thr Met Lys Gly Leu Val Trp Leu Leu
                245                 250                 255 tgt gtt tat ggg gtg cca ttg ctc att gtg aac ggt ttt ctt gtg acc    816
Cys Val Tyr Gly Val Pro Leu Leu Ile Val Asn Gly Phe Leu Val Thr
            260                 265                 270 atc aca tat ctg cag cac aca cac tat gcc ttg cct cac tat gat tca    864
Ile Thr Tyr Leu Gln His Thr His Tyr Ala Leu Pro His Tyr Asp Ser
        275                 280                 285 tca gaa tgg gat tgg ctg agg ggt gct ttg gca act atg gac aga gat    912
Ser Glu Trp Asp Trp Leu Arg Gly Ala Leu Ala Thr Met Asp Arg Asp
    290                 295                 300 tat ggg att ctg aac aag gtg ttt cac cac ata act gat act cat gtg    960
Tyr Gly Ile Leu Asn Lys Val Phe His His Ile Thr Asp Thr His Val
305                 310                 315                 320 gct cac cat ctt ttc tct aca atg cca cat tac cat gca acg gag gca   1008
Ala His His Leu Phe Ser Thr Met Pro His Tyr His Ala Thr Glu Ala
                325                 330                 335 acc aat gca atg aag cca ata ttg ggt gag tac tac cga ttt gat gac   1056
Thr Asn Ala Met Lys Pro Ile Leu Gly Glu Tyr Tyr Arg Phe Asp Asp
            340                 345                 350 aca cca ttt tac aag gca ctg tgg aga gaa gca aga gag tgc ctc tat   1104
Thr Pro Phe Tyr Lys Ala Leu Trp Arg Glu Ala Arg Glu Cys Leu Tyr
        355                 360                 365 gtg gag cca gat gaa gga aca tcc gag aag ggc gtg tat tgg tac agg   1152
Val Glu Pro Asp Glu Gly Thr Ser Glu Lys Gly Val Tyr Trp Tyr Arg
    370                 375                 380 aac aag tat tga                                                   1164
Asn Lys Tyr
385
```

<210> SEQ ID NO 2
<211> LENGTH: 387
<212> TYPE: PRT
<213> ORGANISM: Glycine max
<220> FEATURE:
<223> OTHER INFORMATION: amino acid sequence of FAD2-1B mutant PI 283327

<400> SEQUENCE: 2

```
Met Gly Leu Ala Lys Glu Thr Ile Met Gly Gly Gly Arg Val Ala
1               5                   10                  15

Lys Val Glu Ile Gln Gln Lys Lys Pro Leu Ser Arg Val Pro Asn Thr
                20                  25                  30

Lys Pro Pro Phe Thr Val Gly Gln Leu Lys Lys Ala Ile Pro Pro His
            35                  40                  45

Cys Phe Gln Arg Ser Leu Leu Thr Ser Leu Ser Tyr Val Val Tyr Asp
        50                  55                  60
```

```
Leu Ser Leu Ala Phe Ile Phe Tyr Ile Ala Thr Thr Tyr Phe His Leu
 65                  70                  75                  80

Leu Pro His Pro Phe Leu Ile Ala Trp Pro Ile Tyr Trp Val Leu
             85                  90                  95

Gln Gly Cys Ile Leu Thr Gly Val Trp Val Ile Ala His Glu Cys Gly
                100                 105                 110

His His Ala Phe Ser Lys Tyr Pro Trp Val Asp Asp Val Val Gly Leu
            115                 120                 125

Thr Val His Ser Ala Leu Leu Val Arg Tyr Phe Ser Trp Lys Ile Ser
        130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Tyr Thr Lys Tyr Leu
                165                 170                 175

Asn Asn Pro Leu Gly Arg Ala Ala Ser Leu Leu Ile Thr Leu Thr Ile
            180                 185                 190

Gly Trp Pro Leu Tyr Leu Ala Phe Asn Val Ser Gly Arg Pro Tyr Asp
        195                 200                 205

Gly Phe Ala Ser His Tyr His Pro Tyr Ala Pro Ile Tyr Ser Asn Arg
210                 215                 220

Glu Arg Leu Leu Ile Tyr Val Ser Asp Val Ala Leu Phe Ser Val Thr
225                 230                 235                 240

Tyr Leu Leu Tyr Arg Val Ala Thr Met Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Tyr Ala Leu Pro His Tyr Asp Ser
        275                 280                 285

Ser Glu Trp Asp Trp Leu Arg Gly Ala Leu Ala Thr Met Asp Arg Asp
290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Thr Glu Ala
                325                 330                 335

Thr Asn Ala Met Lys Pro Ile Leu Gly Glu Tyr Tyr Arg Phe Asp Asp
            340                 345                 350

Thr Pro Phe Tyr Lys Ala Leu Trp Arg Glu Ala Arg Glu Cys Leu Tyr
        355                 360                 365

Val Glu Pro Asp Glu Gly Thr Ser Glu Lys Gly Val Tyr Trp Tyr Arg
370                 375                 380

Asn Lys Tyr
385

<210> SEQ ID NO 3
<211> LENGTH: 1164
<212> TYPE: DNA
<213> ORGANISM: Glycine max
<220> FEATURE:
<221> NAME/KEY: CDS
<222> LOCATION: (1)..(1164)
<223> OTHER INFORMATION: nucleotide sequence of FAD2-1B mutant PI
      567189A
<220> FEATURE:
<221> NAME/KEY: mutation
<222> LOCATION: (66)..(66)
<223> OTHER INFORMATION: G to A mutation (silent mutation)
<220> FEATURE:
```

```
<221> NAME/KEY: mutation
<222> LOCATION: (257)..(257)
<223> OTHER INFORMATION: C to T mutation resulting in an amino acid
      substitution of Serine to Phenylalanine at amino acid 86
<220> FEATURE:
<221> NAME/KEY: mutation
<222> LOCATION: (376)..(376)
<223> OTHER INFORMATION: A to G mutation resulting in an amino acid
      substitution of Methionine to Valine at amino acid 126
<220> FEATURE:
<221> NAME/KEY: mutation
<222> LOCATION: (428)..(428)
<223> OTHER INFORMATION: T to C mutation resulting in corresponding
      amino acid substitution of Isoleucine to Threonine at amino acid
      143
<220> FEATURE:
<221> NAME/KEY: mutation
<222> LOCATION: (657)..(657)
<223> OTHER INFORMATION: C to T mutation (silent mutation)
<220> FEATURE:
<221> NAME/KEY: mutation
<222> LOCATION: (669)..(669)
<223> OTHER INFORMATION: T to C mutation (silent mutation)
<220> FEATURE:
<221> NAME/KEY: mutation
<222> LOCATION: (682)..(682)
<223> OTHER INFORMATION: T to C mutation (silent mutation)
<220> FEATURE:
<221> NAME/KEY: mutation
<222> LOCATION: (918)..(918)
<223> OTHER INFORMATION: A to G mutation (silent mutation)

<400> SEQUENCE: 3 atg ggt cta gca aag gaa aca ata atg gga ggt gga ggc cgt gtg gcc      48
Met Gly Leu Ala Lys Glu Thr Ile Met Gly Gly Gly Gly Arg Val Ala
1               5                   10                  15 aaa gtt gaa att cag caa aag aag cct ctc tca agg gtt cca aac aca      96
Lys Val Glu Ile Gln Gln Lys Lys Pro Leu Ser Arg Val Pro Asn Thr
                20                  25                  30 aag cca cca ttc act gtt ggc caa ctc aag aaa gcc att cca ccg cac     144
Lys Pro Pro Phe Thr Val Gly Gln Leu Lys Lys Ala Ile Pro Pro His
            35                  40                  45 tgc ttt cag cgt tcc ctc ctc act tca ttg tcc tat gtt gtt tat gac     192
Cys Phe Gln Arg Ser Leu Leu Thr Ser Leu Ser Tyr Val Val Tyr Asp
    50                  55                  60 ctt tca ttg gct ttc att ttc tac att gcc acc acc tac ttc cac ctc     240
Leu Ser Leu Ala Phe Ile Phe Tyr Ile Ala Thr Thr Tyr Phe His Leu
65                  70                  75                  80 ctc cct cac ccc ttt ttc ctc att gca tgg cca atc tat tgg gtt ctc     288
Leu Pro His Pro Phe Phe Leu Ile Ala Trp Pro Ile Tyr Trp Val Leu
                85                  90                  95 caa ggt tgc att ctt act ggc gtg tgg gtg att gct cac gag tgt ggt     336
Gln Gly Cys Ile Leu Thr Gly Val Trp Val Ile Ala His Glu Cys Gly
                100                 105                 110 cac cat gcc ttc agc aag tac cca tgg gtt gat gat gtt gtg ggt ttg     384
His His Ala Phe Ser Lys Tyr Pro Trp Val Asp Asp Val Val Gly Leu
            115                 120                 125 acc gtt cac tca gca ctt tta gtc cct tat ttc tca tgg aaa aca agc     432
Thr Val His Ser Ala Leu Leu Val Pro Tyr Phe Ser Trp Lys Thr Ser
    130                 135                 140 cat cgc cgc cac cac tcc aac acg ggt tcc ctt gac cgt gat gaa gtg     480
His Arg Arg His His Ser Asn Thr Gly Ser Leu Asp Arg Asp Glu Val
145                 150                 155                 160 ttt gtc cca aaa cca aaa tcc aaa gtt gca tgg tac acc aag tac ctg     528
Phe Val Pro Lys Pro Lys Ser Lys Val Ala Trp Tyr Thr Lys Tyr Leu
                165                 170                 175 aac aac cct cta gga agg gct gct tct ctt ctc atc aca ctc aca ata     576
Asn Asn Pro Leu Gly Arg Ala Ala Ser Leu Leu Ile Thr Leu Thr Ile
```

```
                                                                     -continued Asn Asn Pro Leu Gly Arg Ala Ala Ser Leu Leu Ile Thr Leu Thr Ile
            180                 185                 190 ggg tgg cct ttg tat tta gcc ttc aat gtc tct ggc aga ccc tat gat        624
Gly Trp Pro Leu Tyr Leu Ala Phe Asn Val Ser Gly Arg Pro Tyr Asp
        195                 200                 205 ggt ttt gct agc cac tac cac cct tat gct cct ata tat tca aac cgt        672
Gly Phe Ala Ser His Tyr His Pro Tyr Ala Pro Ile Tyr Ser Asn Arg
    210                 215                 220 gag agg ctt ctg atc tat gtc tct gat gtt gct ttg ttt tct gtg act        720
Glu Arg Leu Leu Ile Tyr Val Ser Asp Val Ala Leu Phe Ser Val Thr
225                 230                 235                 240 tac ttg ctc tac cgt gtt gca act atg aaa ggg ttg gtt tgg ctg cta        768
Tyr Leu Leu Tyr Arg Val Ala Thr Met Lys Gly Leu Val Trp Leu Leu
                245                 250                 255 tgt gtt tat ggg gtg cca ttg ctc att gtg aac ggt ttt ctt gtg acc        816
Cys Val Tyr Gly Val Pro Leu Leu Ile Val Asn Gly Phe Leu Val Thr
            260                 265                 270 atc aca tat ctg cag cac aca cac tat gcc ttg cct cac tat gat tca        864
Ile Thr Tyr Leu Gln His Thr His Tyr Ala Leu Pro His Tyr Asp Ser
        275                 280                 285 tca gaa tgg gat tgg ctg agg ggt gct ttg gca act atg gac aga gat        912
Ser Glu Trp Asp Trp Leu Arg Gly Ala Leu Ala Thr Met Asp Arg Asp
    290                 295                 300 tat ggg att ctg aac aag gtg ttt cac cac ata act gat act cat gtg        960
Tyr Gly Ile Leu Asn Lys Val Phe His His Ile Thr Asp Thr His Val
305                 310                 315                 320 gct cac cat ctt ttc tct aca atg cca cat tac cat gca acg gag gca       1008
Ala His His Leu Phe Ser Thr Met Pro His Tyr His Ala Thr Glu Ala
                325                 330                 335 acc aat gca atg aag cca ata ttg ggt gag tac tac cga ttt gat gac       1056
Thr Asn Ala Met Lys Pro Ile Leu Gly Glu Tyr Tyr Arg Phe Asp Asp
            340                 345                 350 aca cca ttt tac aag gca ctg tgg aga gaa gca aga gag tgc ctc tat       1104
Thr Pro Phe Tyr Lys Ala Leu Trp Arg Glu Ala Arg Glu Cys Leu Tyr
        355                 360                 365 gtg gag cca gat gaa gga aca tcc gag aag ggc gtg tat tgg tac agg       1152
Val Glu Pro Asp Glu Gly Thr Ser Glu Lys Gly Val Tyr Trp Tyr Arg
    370                 375                 380 aac aag tat tga                                                       1164
Asn Lys Tyr
385

<210> SEQ ID NO 4
<211> LENGTH: 387
<212> TYPE: PRT
<213> ORGANISM: Glycine max
<220> FEATURE:
<223> OTHER INFORMATION: amino acid sequence of FAD2-1B mutant PI
      567189A

<400> SEQUENCE: 4

Met Gly Leu Ala Lys Glu Thr Ile Met Gly Gly Gly Arg Val Ala
1               5                   10                  15

Lys Val Glu Ile Gln Gln Lys Lys Pro Leu Ser Arg Val Pro Asn Thr
            20                  25                  30

Lys Pro Pro Phe Thr Val Gly Gln Leu Lys Lys Ala Ile Pro Pro His
        35                  40                  45

Cys Phe Gln Arg Ser Leu Leu Thr Ser Leu Ser Tyr Val Val Tyr Asp
    50                  55                  60

Leu Ser Leu Ala Phe Ile Phe Tyr Ile Ala Thr Thr Tyr Phe His Leu
```

```
                65                  70                  75                  80
Leu Pro His Pro Phe Phe Leu Ile Ala Trp Pro Ile Tyr Trp Val Leu
                    85                  90                  95

Gln Gly Cys Ile Leu Thr Gly Val Trp Val Ile Ala His Glu Cys Gly
                100                 105                 110

His His Ala Phe Ser Lys Tyr Pro Trp Val Asp Asp Val Val Gly Leu
                115                 120                 125

Thr Val His Ser Ala Leu Leu Val Pro Tyr Phe Ser Trp Lys Thr Ser
            130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Tyr Thr Lys Tyr Leu
                165                 170                 175

Asn Asn Pro Leu Gly Arg Ala Ala Ser Leu Leu Ile Thr Leu Thr Ile
                180                 185                 190

Gly Trp Pro Leu Tyr Leu Ala Phe Asn Val Ser Gly Arg Pro Tyr Asp
            195                 200                 205

Gly Phe Ala Ser His Tyr His Pro Tyr Ala Pro Ile Tyr Ser Asn Arg
        210                 215                 220

Glu Arg Leu Leu Ile Tyr Val Ser Asp Val Ala Leu Phe Ser Val Thr
225                 230                 235                 240

Tyr Leu Leu Tyr Arg Val Ala Thr Met Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Tyr Ala Leu Pro His Tyr Asp Ser
        275                 280                 285

Ser Glu Trp Asp Trp Leu Arg Gly Ala Leu Ala Thr Met Asp Arg Asp
    290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Thr Glu Ala
                325                 330                 335

Thr Asn Ala Met Lys Pro Ile Leu Gly Glu Tyr Tyr Arg Phe Asp Asp
            340                 345                 350

Thr Pro Phe Tyr Lys Ala Leu Trp Arg Glu Ala Arg Glu Cys Leu Tyr
        355                 360                 365

Val Glu Pro Asp Glu Gly Thr Ser Glu Lys Gly Val Tyr Trp Tyr Arg
    370                 375                 380

Asn Lys Tyr
385

<210> SEQ ID NO 5
<211> LENGTH: 1357
<212> TYPE: DNA
<213> ORGANISM: Glycine max
<220> FEATURE:
<221> NAME/KEY: CDS
<222> LOCATION: (74)..(1237)

<400> SEQUENCE: 5
tatttgcatt gtattgatag cccctccatt cccaagagta taaaactgca tcgaataata     60
caagccacta ggc atg ggt cta gca aag gaa aca aca atg gga ggt aga       109
              Met Gly Leu Ala Lys Glu Thr Thr Met Gly Gly Arg
                1               5                   10
```

```
ggt cgt gtg gcc aaa gtg gaa gtt caa ggg aag aag cct ctc tca agg      157
Gly Arg Val Ala Lys Val Glu Val Gln Gly Lys Lys Pro Leu Ser Arg
        15                  20                  25 gtt cca aac aca aag cca cca ttc act gtt ggc caa ctc aag aaa gca      205
Val Pro Asn Thr Lys Pro Pro Phe Thr Val Gly Gln Leu Lys Lys Ala
 30                  35                  40 att cca cca cac tgc ttt cag cgc tcc ctc ctc act tca ttc tcc tat      253
Ile Pro Pro His Cys Phe Gln Arg Ser Leu Leu Thr Ser Phe Ser Tyr
 45                  50                  55                  60 gtt gtt tat gac ctt tca ttt gcc ttc att ttc tac att gcc acc acc      301
Val Val Tyr Asp Leu Ser Phe Ala Phe Ile Phe Tyr Ile Ala Thr Thr
                 65                  70                  75 tac ttc cac ctc ctt cct caa ccc ttt tcc ctc att gca tgg cca atc      349
Tyr Phe His Leu Leu Pro Gln Pro Phe Ser Leu Ile Ala Trp Pro Ile
                     80                  85                  90 tat tgg gtt ctc caa ggt tgc ctt ctc act ggt gtg tgg gtg att gct      397
Tyr Trp Val Leu Gln Gly Cys Leu Leu Thr Gly Val Trp Val Ile Ala
         95                  100                 105 cac gag tgt ggt cac cat gcc ttc agc aag tac caa tgg gtt gat gat      445
His Glu Cys Gly His His Ala Phe Ser Lys Tyr Gln Trp Val Asp Asp
     110                 115                 120 gtt gtg ggt ttg acc ctt cac tca aca ctt tta gtc cct tat ttc tca      493
Val Val Gly Leu Thr Leu His Ser Thr Leu Leu Val Pro Tyr Phe Ser
125                 130                 135                 140 tgg aaa ata agc cat cgc cgc cat cac tcc aac aca ggt tcc ctt gac      541
Trp Lys Ile Ser His Arg Arg His His Ser Asn Thr Gly Ser Leu Asp
                 145                 150                 155 cgt gat gaa gtg ttt gtc cca aaa cca aaa tcc aaa gtt gca tgg ttt      589
Arg Asp Glu Val Phe Val Pro Lys Pro Lys Ser Lys Val Ala Trp Phe
                     160                 165                 170 tcc aag tac tta aac aac cct cta gga agg gct gtt tct ctt ctc gtc      637
Ser Lys Tyr Leu Asn Asn Pro Leu Gly Arg Ala Val Ser Leu Leu Val
         175                 180                 185 aca ctc aca ata ggg tgg cct atg tat tta gcc ttc aat gtc tct ggt      685
Thr Leu Thr Ile Gly Trp Pro Met Tyr Leu Ala Phe Asn Val Ser Gly
     190                 195                 200 aga ccc tat gat agt ttt gca agc cac tac cac cct tat gct ccc ata      733
Arg Pro Tyr Asp Ser Phe Ala Ser His Tyr His Pro Tyr Ala Pro Ile
205                 210                 215                 220 tat tct aac cgt gag agg ctt ctg atc tat gtc tct gat gtt gct ttg      781
Tyr Ser Asn Arg Glu Arg Leu Leu Ile Tyr Val Ser Asp Val Ala Leu
                 225                 230                 235 ttt tct gtg act tac tct ctc tac cgt gtt gca acc ctg aaa ggg ttg      829
Phe Ser Val Thr Tyr Ser Leu Tyr Arg Val Ala Thr Leu Lys Gly Leu
                     240                 245                 250 gtt tgg ctg cta tgt gtt tat ggg gtg cct ttg ctc att gtg aac ggt      877
Val Trp Leu Leu Cys Val Tyr Gly Val Pro Leu Leu Ile Val Asn Gly
         255                 260                 265 ttt ctt gtg act atc aca tat ttg cag cac aca cac ttt gcc ttg cct      925
Phe Leu Val Thr Ile Thr Tyr Leu Gln His Thr His Phe Ala Leu Pro
     270                 275                 280 cat tac gat tca tca gaa tgg gac tgg ctg aag gga gct ttg gca act      973
His Tyr Asp Ser Ser Glu Trp Asp Trp Leu Lys Gly Ala Leu Ala Thr
285                 290                 295                 300 atg gac aga gat tat ggg att ctg aac aag gtg ttt cat cac ata act     1021
Met Asp Arg Asp Tyr Gly Ile Leu Asn Lys Val Phe His His Ile Thr
                 305                 310                 315 gat act cat gtg gct cac cat ctc ttc tct aca atg cca cat tac cat     1069
Asp Thr His Val Ala His His Leu Phe Ser Thr Met Pro His Tyr His
                     320                 325                 330
```

```
gca atg gag gca acc aat gca atc aag cca ata ttg ggt gag tac tac    1117
Ala Met Glu Ala Thr Asn Ala Ile Lys Pro Ile Leu Gly Glu Tyr Tyr
    335                 340                 345 caa ttt gat gac aca cca ttt tac aag gca ctg tgg aga gaa gcg aga    1165
Gln Phe Asp Asp Thr Pro Phe Tyr Lys Ala Leu Trp Arg Glu Ala Arg
350                 355                 360 gag tgc ctc tat gtg gag cca gat gaa gga aca tcc gag aag ggc gtg    1213
Glu Cys Leu Tyr Val Glu Pro Asp Glu Gly Thr Ser Glu Lys Gly Val
365                 370                 375                 380 tat tgg tac agg aac aag tat tga tggagcaacc aatgggccat agtgggagtt   1267
Tyr Trp Tyr Arg Asn Lys Tyr
            385 atggaagttt tgtcatgtat tagtacataa ttagtagaat gttataaata agtggatttg   1327 ccgcgtaatg actttgtgtg tattgtgaaa                                   1357

<210> SEQ ID NO 6
<211> LENGTH: 387
<212> TYPE: PRT
<213> ORGANISM: Glycine max

<400> SEQUENCE: 6

Met Gly Leu Ala Lys Glu Thr Thr Met Gly Gly Arg Gly Arg Val Ala
1               5                   10                  15

Lys Val Glu Val Gln Gly Lys Lys Pro Leu Ser Arg Val Pro Asn Thr
            20                  25                  30

Lys Pro Pro Phe Thr Val Gly Gln Leu Lys Lys Ala Ile Pro Pro His
        35                  40                  45

Cys Phe Gln Arg Ser Leu Leu Thr Ser Phe Ser Tyr Val Val Tyr Asp
    50                  55                  60

Leu Ser Phe Ala Phe Ile Phe Tyr Ile Ala Thr Thr Tyr Phe His Leu
65                  70                  75                  80

Leu Pro Gln Pro Phe Ser Leu Ile Ala Trp Pro Ile Tyr Trp Val Leu
                85                  90                  95

Gln Gly Cys Leu Leu Thr Gly Val Trp Val Ile Ala His Glu Cys Gly
            100                 105                 110

His His Ala Phe Ser Lys Tyr Gln Trp Val Asp Asp Val Val Gly Leu
        115                 120                 125

Thr Leu His Ser Thr Leu Leu Val Pro Tyr Phe Ser Trp Lys Ile Ser
    130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
            180                 185                 190

Gly Trp Pro Met Tyr Leu Ala Phe Asn Val Ser Gly Arg Pro Tyr Asp
        195                 200                 205

Ser Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240

Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
            260                 265                 270
```

```
Ile Thr Tyr Leu Gln His Thr His Phe Ala Leu Pro His Tyr Asp Ser
        275                 280                 285

Ser Glu Trp Asp Trp Leu Lys Gly Ala Leu Ala Thr Met Asp Arg Asp
        290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Met Glu Ala
                325                 330                 335

Thr Asn Ala Ile Lys Pro Ile Leu Gly Glu Tyr Tyr Gln Phe Asp Asp
                340                 345                 350

Thr Pro Phe Tyr Lys Ala Leu Trp Arg Glu Ala Arg Glu Cys Leu Tyr
                355                 360                 365

Val Glu Pro Asp Glu Gly Thr Ser Glu Lys Val Tyr Trp Tyr Arg
        370                 375                 380

Asn Lys Tyr
385

<210> SEQ ID NO 7
<211> LENGTH: 1164
<212> TYPE: DNA
<213> ORGANISM: Glycine max
<220> FEATURE:
<221> NAME/KEY: CDS
<222> LOCATION: (1)..(1104)
<220> FEATURE:
<221> NAME/KEY: mutation
<222> LOCATION: (350)..(350)
<223> OTHER INFORMATION: X to A mutation resulting in a corresponding
      amino acid subsituttion of Serine to Asparagine at amino acid
      position 117

<400> SEQUENCE: 7 atg ggt cta gca aag gaa aca aca atg gga ggt aga ggt cgt gtg gcc      48
Met Gly Leu Ala Lys Glu Thr Thr Met Gly Gly Arg Gly Arg Val Ala
1               5                   10                  15 aaa gtg gaa gtt caa ggg aag aag cct ctc tca agg gtt cca aac aca      96
Lys Val Glu Val Gln Gly Lys Lys Pro Leu Ser Arg Val Pro Asn Thr
                20                  25                  30 aag cca cca ttc act gtt ggc caa ctc aag aaa gca att cca cca cac     144
Lys Pro Pro Phe Thr Val Gly Gln Leu Lys Lys Ala Ile Pro Pro His
            35                  40                  45 tgc ttt cag cgc tcc ctc ctc act tca ttc tcc tat gtt gtt tat gac     192
Cys Phe Gln Arg Ser Leu Leu Thr Ser Phe Ser Tyr Val Val Tyr Asp
        50                  55                  60 ctt tca ttt gcc ttc att ttc tac att gcc acc acc tac ttc cac ctc     240
Leu Ser Phe Ala Phe Ile Phe Tyr Ile Ala Thr Thr Tyr Phe His Leu
65                  70                  75                  80 ctt cct caa ccc ttt tcc ctc att gca tgg cca atc tat tgg gtt ctc     288
Leu Pro Gln Pro Phe Ser Leu Ile Ala Trp Pro Ile Tyr Trp Val Leu
                85                  90                  95 caa ggt tgc ctt ctc act ggt gtg tgg gtg att gct cac gag tgt ggt     336
Gln Gly Cys Leu Leu Thr Gly Val Trp Val Ile Ala His Glu Cys Gly
                100                 105                 110 cac cat gcc ttc aac aag tac caa tgg gtt gat gat gtt gtg ggt ttg     384
His His Ala Phe Asn Lys Tyr Gln Trp Val Asp Asp Val Val Gly Leu
            115                 120                 125 acc ctt cac tca aca ctt tta gtc cct tat ttc tca tgg aaa ata agc     432
Thr Leu His Ser Thr Leu Leu Val Pro Tyr Phe Ser Trp Lys Ile Ser
        130                 135                 140 cat cgc cgc cat cac tcc aac aca ggt tcc ctt gac cgt gat gaa gtg     480
```

```
His Arg Arg His His Ser Asn Thr Gly Ser Leu Asp Arg Asp Glu Val
145                 150                 155                 160 ttt gtc cca aaa cca aaa tcc aaa gtt gca tgg ttt tcc aag tac tta      528
Phe Val Pro Lys Pro Lys Ser Lys Val Ala Trp Phe Ser Lys Tyr Leu
                165                 170                 175 aac aac cct cta gga agg gct gtt tct ctt ctc gtc aca ctc aca ata      576
Asn Asn Pro Leu Gly Arg Ala Val Ser Leu Leu Val Thr Leu Thr Ile
            180                 185                 190 ggg tgg cct atg tat tta gcc ttc aat gtc tct ggt aga ccc tat gat      624
Gly Trp Pro Met Tyr Leu Ala Phe Asn Val Ser Gly Arg Pro Tyr Asp
        195                 200                 205 agt ttt gca agc cac tac cac cct tat gct ccc ata tat tct aac cgt      672
Ser Phe Ala Ser His Tyr His Pro Tyr Ala Pro Ile Tyr Ser Asn Arg
    210                 215                 220 gag agg ctt ctg atc tat gtc tct gat gtt gct ttg ttt tct gtg act      720
Glu Arg Leu Leu Ile Tyr Val Ser Asp Val Ala Leu Phe Ser Val Thr
225                 230                 235                 240 tac tct ctc tac cgt gtt gca acc ctg aaa ggg ttg gtt tgg ctg cta      768
Tyr Ser Leu Tyr Arg Val Ala Thr Leu Lys Gly Leu Val Trp Leu Leu
                245                 250                 255 tgt gtt tat ggg gtg cct ttg ctc att gtg aac ggt ttt ctt gtg act      816
Cys Val Tyr Gly Val Pro Leu Leu Ile Val Asn Gly Phe Leu Val Thr
            260                 265                 270 atc aca tat ttg cag cac aca cac ttt gcc ttg cct cat tac gat tca      864
Ile Thr Tyr Leu Gln His Thr His Phe Ala Leu Pro His Tyr Asp Ser
        275                 280                 285 tca gaa tgg gac tgg ctg aag gga gct ttg gca act atg gac aga gat      912
Ser Glu Trp Asp Trp Leu Lys Gly Ala Leu Ala Thr Met Asp Arg Asp
    290                 295                 300 tat ggg att ctg aac aag gtg ttt cat cac ata act gat act cat gtg      960
Tyr Gly Ile Leu Asn Lys Val Phe His His Ile Thr Asp Thr His Val
305                 310                 315                 320 gct cac cat ctc ttc tct aca atg cca cat tac cat gca atg gag gca     1008
Ala His His Leu Phe Ser Thr Met Pro His Tyr His Ala Met Glu Ala
                325                 330                 335 acc aat gca atc aag cca ata ttg ggt gag tac tac caa ttt gat gac     1056
Thr Asn Ala Ile Lys Pro Ile Leu Gly Glu Tyr Tyr Gln Phe Asp Asp
            340                 345                 350 aca cca ttt tac aag gca ctg tgg aga gaa gcg aga gag tgc ctc tat     1104
Thr Pro Phe Tyr Lys Ala Leu Trp Arg Glu Ala Arg Glu Cys Leu Tyr
        355                 360                 365 gtggagccag atgaaggaac atccgagaag ggcgtgtatt ggtacaggaa caagtattga   1164

<210> SEQ ID NO 8
<211> LENGTH: 368
<212> TYPE: PRT
<213> ORGANISM: Glycine max

<400> SEQUENCE: 8

Met Gly Leu Ala Lys Glu Thr Thr Met Gly Gly Arg Gly Arg Val Ala
1               5                   10                  15

Lys Val Glu Val Gln Gly Lys Lys Pro Leu Ser Arg Val Pro Asn Thr
                20                  25                  30

Lys Pro Pro Phe Thr Val Gly Gln Leu Lys Lys Ala Ile Pro Pro His
            35                  40                  45

Cys Phe Gln Arg Ser Leu Leu Thr Ser Phe Ser Tyr Val Val Tyr Asp
        50                  55                  60

Leu Ser Phe Ala Phe Ile Phe Tyr Ile Ala Thr Thr Tyr Phe His Leu
65                  70                  75                  80
```

```
Leu Pro Gln Pro Phe Ser Leu Ile Ala Trp Pro Ile Tyr Trp Val Leu
                85                  90                  95

Gln Gly Cys Leu Leu Thr Gly Val Trp Val Ile Ala His Glu Cys Gly
            100                 105                 110

His His Ala Phe Asn Lys Tyr Gln Trp Val Asp Asp Val Val Gly Leu
        115                 120                 125

Thr Leu His Ser Thr Leu Leu Val Pro Tyr Phe Ser Trp Lys Ile Ser
    130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
            180                 185                 190

Gly Trp Pro Met Tyr Leu Ala Phe Asn Val Ser Gly Arg Pro Tyr Asp
        195                 200                 205

Ser Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240

Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Phe Ala Leu Pro His Tyr Asp Ser
        275                 280                 285

Ser Glu Trp Asp Trp Leu Lys Gly Ala Leu Ala Thr Met Asp Arg Asp
    290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Met Glu Ala
                325                 330                 335

Thr Asn Ala Ile Lys Pro Ile Leu Gly Glu Tyr Tyr Gln Phe Asp Asp
            340                 345                 350

Thr Pro Phe Tyr Lys Ala Leu Trp Arg Glu Ala Arg Glu Cys Leu Tyr
        355                 360                 365

<210> SEQ ID NO 9
<211> LENGTH: 1164
<212> TYPE: DNA
<213> ORGANISM: Glycine max
<220> FEATURE:
<221> NAME/KEY: CDS
<222> LOCATION: (1)..(1104)

<400> SEQUENCE: 9 atg ggt cta gca aag gaa aca aca atg gga ggt aga ggt cgt gtg gcc      48
Met Gly Leu Ala Lys Glu Thr Thr Met Gly Gly Arg Gly Arg Val Ala
1               5                   10                  15 aaa gtg gaa gtt caa ggg aag aag cct ctc tca agg gtt cca aac aca      96
Lys Val Glu Val Gln Gly Lys Lys Pro Leu Ser Arg Val Pro Asn Thr
            20                  25                  30 aag cca cca ttc act gtt ggc caa ctc aag aaa gca att cca cca cac     144
Lys Pro Pro Phe Thr Val Gly Gln Leu Lys Lys Ala Ile Pro Pro His
        35                  40                  45 tgc ttt cag cgc tcc ctc ctc act tca ttc tcc tat gtt gtt tat gac     192
```

```
          Cys Phe Gln Arg Ser Leu Leu Thr Ser Phe Ser Tyr Val Val Tyr Asp
              50                  55                  60 ctt tca ttt gcc ttc att ttc tac att gcc acc acc tac ttc cac ctc        240
Leu Ser Phe Ala Phe Ile Phe Tyr Ile Ala Thr Thr Tyr Phe His Leu
 65                  70                  75                  80 ctt cct caa ccc ttt tcc ctc att gca tgg cca atc tat tgg gtt ctc        288
Leu Pro Gln Pro Phe Ser Leu Ile Ala Trp Pro Ile Tyr Trp Val Leu
                 85                  90                  95 caa ggt tgc ctt ctc act ggt gtg tgg gtg att gct cac gag tgt ggt        336
Gln Gly Cys Leu Leu Thr Gly Val Trp Val Ile Ala His Glu Cys Gly
            100                 105                 110 cac cat gcc ttc agc aag tac caa tgg gtt gat gat gtt gtg ggt ttg        384
His His Ala Phe Ser Lys Tyr Gln Trp Val Asp Asp Val Val Gly Leu
            115                 120                 125 acc ctt cac tca aca ctt tta gtc cct tat ttc tca tgg aaa ata agc        432
Thr Leu His Ser Thr Leu Leu Val Pro Tyr Phe Ser Trp Lys Ile Ser
        130                 135                 140 cat cgc cgc cat cac tcc aac aca ggt tcc ctt gac cgt gat gaa gtg        480
His Arg Arg His His Ser Asn Thr Gly Ser Leu Asp Arg Asp Glu Val
145                 150                 155                 160 ttt gtc cca aaa cca aaa tcc aaa gtt gca tgg ttt tcc aag tac tta        528
Phe Val Pro Lys Pro Lys Ser Lys Val Ala Trp Phe Ser Lys Tyr Leu
                165                 170                 175 aac aac cct cta gga agg gct gtt tct ctt ctc gtc aca ctc aca ata        576
Asn Asn Pro Leu Gly Arg Ala Val Ser Leu Leu Val Thr Leu Thr Ile
            180                 185                 190 ggg tgg cct atg tat tta gcc ttc aat gtc tct ggt aga ccc tat gat        624
Gly Trp Pro Met Tyr Leu Ala Phe Asn Val Ser Gly Arg Pro Tyr Asp
        195                 200                 205 agt ttt gca agc cac tac cac cct tat gct ccc ata tat tct aac cgt        672
Ser Phe Ala Ser His Tyr His Pro Tyr Ala Pro Ile Tyr Ser Asn Arg
    210                 215                 220 gag agg ctt ctg atc tat gtc tct gat gtt gct ttg ttt tct gtg act        720
Glu Arg Leu Leu Ile Tyr Val Ser Asp Val Ala Leu Phe Ser Val Thr
225                 230                 235                 240 tac tct ctc tac cgt gtt gca acc ctg aaa ggg ttg gtt tgg ctg cta        768
Tyr Ser Leu Tyr Arg Val Ala Thr Leu Lys Gly Leu Val Trp Leu Leu
                245                 250                 255 tgt gtt tat ggg gtg cct ttg ctc att gtg aac ggt ttt ctt gtg act        816
Cys Val Tyr Gly Val Pro Leu Leu Ile Val Asn Gly Phe Leu Val Thr
            260                 265                 270 atc aca tat ttg cag cac aca cac ttt gcc ttg cct cat tac gat tca        864
Ile Thr Tyr Leu Gln His Thr His Phe Ala Leu Pro His Tyr Asp Ser
        275                 280                 285 tca gaa tgg gac tgg ctg aag gga gct ttg gca act atg gac aga gat        912
Ser Glu Trp Asp Trp Leu Lys Gly Ala Leu Ala Thr Met Asp Arg Asp
    290                 295                 300 tat ggg att ctg aac aag gtg ttt cat cac ata act gat act cat gtg        960
Tyr Gly Ile Leu Asn Lys Val Phe His His Ile Thr Asp Thr His Val
305                 310                 315                 320 gct cac cat ctc ttc tct aca atg cca cat tac cat gca atg gag gca       1008
Ala His His Leu Phe Ser Thr Met Pro His Tyr His Ala Met Glu Ala
                325                 330                 335 acc aat gca atc aag cca ata ttg ggt gag tac tac caa ttt gat gac       1056
Thr Asn Ala Ile Lys Pro Ile Leu Gly Glu Tyr Tyr Gln Phe Asp Asp
            340                 345                 350 aca cca ttt tac aag gca ctg tgg aga gaa gcg aga gag tgc ctc tat       1104
Thr Pro Phe Tyr Lys Ala Leu Trp Arg Glu Ala Arg Glu Cys Leu Tyr
        355                 360                 365
```
gtggagccag atgaaggaac atccgagaag ggcgtgtatt ggtacaggaa caagtattga    1164

<210> SEQ ID NO 10
<211> LENGTH: 368
<212> TYPE: PRT
<213> ORGANISM: Glycine max

<400> SEQUENCE: 10

```
Met Gly Leu Ala Lys Glu Thr Thr Met Gly Gly Arg Gly Arg Val Ala
1               5                   10                  15

Lys Val Glu Val Gln Gly Lys Lys Pro Leu Ser Arg Val Pro Asn Thr
            20                  25                  30

Lys Pro Pro Phe Thr Val Gly Gln Leu Lys Lys Ala Ile Pro Pro His
        35                  40                  45

Cys Phe Gln Arg Ser Leu Leu Thr Ser Phe Ser Tyr Val Val Tyr Asp
    50                  55                  60

Leu Ser Phe Ala Phe Ile Phe Tyr Ile Ala Thr Thr Tyr Phe His Leu
65                  70                  75                  80

Leu Pro Gln Pro Phe Ser Leu Ile Ala Trp Pro Ile Tyr Trp Val Leu
                85                  90                  95

Gln Gly Cys Leu Leu Thr Gly Val Trp Val Ile Ala His Glu Cys Gly
            100                 105                 110

His His Ala Phe Ser Lys Tyr Gln Trp Val Asp Asp Val Val Gly Leu
        115                 120                 125

Thr Leu His Ser Thr Leu Leu Val Pro Tyr Phe Ser Trp Lys Ile Ser
    130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
            180                 185                 190

Gly Trp Pro Met Tyr Leu Ala Phe Asn Val Ser Gly Arg Pro Tyr Asp
        195                 200                 205

Ser Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240

Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Phe Ala Leu Pro His Tyr Asp Ser
        275                 280                 285

Ser Glu Trp Asp Trp Leu Lys Gly Ala Leu Ala Thr Met Asp Arg Asp
    290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Met Glu Ala
                325                 330                 335

Thr Asn Ala Ile Lys Pro Ile Leu Gly Glu Tyr Tyr Gln Phe Asp Asp
            340                 345                 350

Thr Pro Phe Tyr Lys Ala Leu Trp Arg Glu Ala Arg Glu Cys Leu Tyr
        355                 360                 365
```

```
<210> SEQ ID NO 11
<211> LENGTH: 1164
<212> TYPE: DNA
<213> ORGANISM: Glycine max
<220> FEATURE:
<221> NAME/KEY: CDS
<222> LOCATION: (1)..(1104)

<400> SEQUENCE: 11 atg ggt cta gca aag gaa aca ata atg gga ggt gga ggc cgt gtg gcc      48
Met Gly Leu Ala Lys Glu Thr Ile Met Gly Gly Gly Gly Arg Val Ala
1               5                   10                  15 aaa gtt gaa att cag cag aag aag cct ctc tca agg gtt cca aac aca      96
Lys Val Glu Ile Gln Gln Lys Lys Pro Leu Ser Arg Val Pro Asn Thr
            20                  25                  30 aag cca cca ttc act gtt ggc caa ctc aag aaa gcc att cca ccg cac     144
Lys Pro Pro Phe Thr Val Gly Gln Leu Lys Lys Ala Ile Pro Pro His
        35                  40                  45 tgc ttt cag cgt tcc ctc ctc act tca ttg tcc tat gtt gtt tat gac     192
Cys Phe Gln Arg Ser Leu Leu Thr Ser Leu Ser Tyr Val Val Tyr Asp
50                  55                  60 ctt tca ttg gct ttc att ttc tac att gcc acc acc tac ttc cac ctc     240
Leu Ser Leu Ala Phe Ile Phe Tyr Ile Ala Thr Thr Tyr Phe His Leu
65                  70                  75                  80 ctc cct cac ccc ttt tcc ctc att gca tgg cca atc tat tgg gtt ctc     288
Leu Pro His Pro Phe Ser Leu Ile Ala Trp Pro Ile Tyr Trp Val Leu
                85                  90                  95 caa ggt tgc att ctt act ggc gtg tgg gtg att gct cac gag tgt ggt     336
Gln Gly Cys Ile Leu Thr Gly Val Trp Val Ile Ala His Glu Cys Gly
            100                 105                 110 cac cat gcc ttc agc aag tac cca tgg gtt gat gat gtt atg ggt ttg     384
His His Ala Phe Ser Lys Tyr Pro Trp Val Asp Asp Val Met Gly Leu
        115                 120                 125 acc gtt cac tca gca ctt tta gtc cct tat ttc tca tgg aaa ata agc     432
Thr Val His Ser Ala Leu Leu Val Pro Tyr Phe Ser Trp Lys Ile Ser
    130                 135                 140 cat cgc cgc cac cac tcc aac acg ggt tcc ctt gac cgt gat gaa gtg     480
His Arg Arg His His Ser Asn Thr Gly Ser Leu Asp Arg Asp Glu Val
145                 150                 155                 160 ttt gtc cca aaa cca aaa tcc aaa gtt gca tgg tac acc aag tac ctg     528
Phe Val Pro Lys Pro Lys Ser Lys Val Ala Trp Tyr Thr Lys Tyr Leu
                165                 170                 175 aac aac cct cta gga agg gct gct tct ctt ctc atc aca ctc aca ata     576
Asn Asn Pro Leu Gly Arg Ala Ala Ser Leu Leu Ile Thr Leu Thr Ile
            180                 185                 190 ggg tgg cct ttg tat tta gcc ttc aat gtc tct gga aga ccc tat gat     624
Gly Trp Pro Leu Tyr Leu Ala Phe Asn Val Ser Gly Arg Pro Tyr Asp
        195                 200                 205 ggt ttt gct agc cac tac cac cct tat gct ccc ata tat tca aat cgt     672
Gly Phe Ala Ser His Tyr His Pro Tyr Ala Pro Ile Tyr Ser Asn Arg
    210                 215                 220 gag agg ctt ttg atc tat gtc tct gat gtt gct ttg ttt tct gtg act     720
Glu Arg Leu Leu Ile Tyr Val Ser Asp Val Ala Leu Phe Ser Val Thr
225                 230                 235                 240 tac ttg ctc tac cgt gtt gca act atg aaa ggg ttg gtt tgg ctg cta     768
Tyr Leu Leu Tyr Arg Val Ala Thr Met Lys Gly Leu Val Trp Leu Leu
                245                 250                 255 tgt gtt tat ggg gtg cca ttg ctc att gtg aac ggt ttt ctt gtg acc     816
Cys Val Tyr Gly Val Pro Leu Leu Ile Val Asn Gly Phe Leu Val Thr
            260                 265                 270
```

```
atc aca tat ctg cag cac aca cac tat gcc ttg cct cac tat gat tca    864
Ile Thr Tyr Leu Gln His Thr His Tyr Ala Leu Pro His Tyr Asp Ser
        275                 280                 285 tca gaa tgg gat tgg ctg agg ggt gct ttg gca act atg gac aga gat    912
Ser Glu Trp Asp Trp Leu Arg Gly Ala Leu Ala Thr Met Asp Arg Asp
    290                 295                 300 tat gga att ctg aac aag gtg ttt cac cac ata act gat act cat gtg    960
Tyr Gly Ile Leu Asn Lys Val Phe His His Ile Thr Asp Thr His Val
305                 310                 315                 320 gct cac cat ctt ttc tct aca atg cca cat tac cat gca acg gag gca   1008
Ala His His Leu Phe Ser Thr Met Pro His Tyr His Ala Thr Glu Ala
                325                 330                 335 acc aat gca atg aag cca ata ttg ggt gag tac tac cga ttt gat gac   1056
Thr Asn Ala Met Lys Pro Ile Leu Gly Glu Tyr Tyr Arg Phe Asp Asp
            340                 345                 350 aca cca ttt tac aag gca ctg tgg aga gaa gca aga gag tgc ctc tat   1104
Thr Pro Phe Tyr Lys Ala Leu Trp Arg Glu Ala Arg Glu Cys Leu Tyr
        355                 360                 365 gtggagccag atgaaggaac atccgagaag ggcgtgtatt ggtacaggaa caagtattga  1164

<210> SEQ ID NO 12
<211> LENGTH: 368
<212> TYPE: PRT
<213> ORGANISM: Glycine max

<400> SEQUENCE: 12

Met Gly Leu Ala Lys Glu Thr Ile Met Gly Gly Gly Arg Val Ala
1               5                   10                  15

Lys Val Glu Ile Gln Gln Lys Lys Pro Leu Ser Arg Val Pro Asn Thr
                20                  25                  30

Lys Pro Pro Phe Thr Val Gly Gln Leu Lys Lys Ala Ile Pro Pro His
            35                  40                  45

Cys Phe Gln Arg Ser Leu Leu Thr Ser Leu Ser Tyr Val Val Tyr Asp
    50                  55                  60

Leu Ser Leu Ala Phe Ile Phe Tyr Ile Ala Thr Thr Tyr Phe His Leu
65                  70                  75                  80

Leu Pro His Pro Phe Ser Leu Ile Ala Trp Pro Ile Tyr Trp Val Leu
                85                  90                  95

Gln Gly Cys Ile Leu Thr Gly Val Trp Val Ile Ala His Glu Cys Gly
            100                 105                 110

His His Ala Phe Ser Lys Tyr Pro Trp Val Asp Asp Val Met Gly Leu
        115                 120                 125

Thr Val His Ser Ala Leu Leu Val Pro Tyr Phe Ser Trp Lys Ile Ser
    130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Tyr Thr Lys Tyr Leu
                165                 170                 175

Asn Asn Pro Leu Gly Arg Ala Ala Ser Leu Leu Ile Thr Leu Thr Ile
            180                 185                 190

Gly Trp Pro Leu Tyr Leu Ala Phe Asn Val Ser Gly Arg Pro Tyr Asp
        195                 200                 205

Gly Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240
```

```
       Tyr Leu Leu Tyr Arg Val Ala Thr Met Lys Gly Leu Val Trp Leu Leu
                       245                 250                 255

Cys Val Tyr Gly Val Pro Leu Leu Ile Val Asn Gly Phe Leu Val Thr
                   260                 265                 270

Ile Thr Tyr Leu Gln His Thr His Tyr Ala Leu Pro His Tyr Asp Ser
                       275                 280                 285

Ser Glu Trp Asp Trp Leu Arg Gly Ala Leu Ala Thr Met Asp Arg Asp
                   290                 295                 300

Tyr Gly Ile Leu Asn Lys Val Phe His His Ile Thr Asp Thr His Val
       305                 310                 315                 320

Ala His His Leu Phe Ser Thr Met Pro His Tyr His Ala Thr Glu Ala
                       325                 330                 335

Thr Asn Ala Met Lys Pro Ile Leu Gly Glu Tyr Tyr Arg Phe Asp Asp
                       340                 345                 350

Thr Pro Phe Tyr Lys Ala Leu Trp Arg Glu Ala Arg Glu Cys Leu Tyr
                       355                 360                 365

<210> SEQ ID NO 13
<211> LENGTH: 22
<212> TYPE: DNA
<213> ORGANISM: Artificial
<220> FEATURE:
<223> OTHER INFORMATION: forward primer for FAD2-1A

<400> SEQUENCE: 13
actgcatcga ataatacaag cc                                              22

<210> SEQ ID NO 14
<211> LENGTH: 19
<212> TYPE: DNA
<213> ORGANISM: Artificial
<220> FEATURE:
<223> OTHER INFORMATION: reverse primer for FAD2-1A

<400> SEQUENCE: 14
tgatattgtc ccgtgcagc                                                  19

<210> SEQ ID NO 15
<211> LENGTH: 20
<212> TYPE: DNA
<213> ORGANISM: Artificial
<220> FEATURE:
<223> OTHER INFORMATION: forward primer for FAD2-1B

<400> SEQUENCE: 15
cccgctgtcc cttttaaact                                                 20

<210> SEQ ID NO 16
<211> LENGTH: 25
<212> TYPE: DNA
<213> ORGANISM: Artificial
<220> FEATURE:
<223> OTHER INFORMATION: reverse primer for FAD2-1B

<400> SEQUENCE: 16
ttacattata gccatggatc gctac                                           25

<210> SEQ ID NO 17
<211> LENGTH: 28
<212> TYPE: DNA
<213> ORGANISM: Artificial
<220> FEATURE:
<223> OTHER INFORMATION: SimpleProbe GmFAD2-1B
```

<400> SEQUENCE: 17
agtcccttat ttctcatgga aaataagc                                              28

<210> SEQ ID NO 18
<211> LENGTH: 22
<212> TYPE: DNA
<213> ORGANISM: Artificial
<220> FEATURE:
<223> OTHER INFORMATION: primer for genotyping reactions

<400> SEQUENCE: 18
actgcatcga ataatacaag cc                                                    22

<210> SEQ ID NO 19
<211> LENGTH: 19
<212> TYPE: DNA
<213> ORGANISM: Artificial
<220> FEATURE:
<223> OTHER INFORMATION: primer for genotyping reactions

<400> SEQUENCE: 19
tgatattgtc ccgtccagc                                                        19

<210> SEQ ID NO 20
<211> LENGTH: 1163
<212> TYPE: DNA
<213> ORGANISM: Glycine max
<220> FEATURE:
<221> NAME/KEY: CDS
<222> LOCATION: (1)..(573)
<220> FEATURE:
<221> NAME/KEY: mutation
<222> LOCATION: (543)..(543)
<223> OTHER INFORMATION: single A is deleted at position 543 or 544
      causing a frame shift of the coding sequence for the FAD2-1A

<400> SEQUENCE: 20

```
atg ggt cta gca aag gaa aca aca atg gga ggt aga ggt cgt gtg gcc        48
Met Gly Leu Ala Lys Glu Thr Thr Met Gly Gly Arg Gly Arg Val Ala
1               5                   10                  15 aaa gtg gaa gtt caa ggg aag aag cct ctc tca agg gtt cca aac aca        96
Lys Val Glu Val Gln Gly Lys Lys Pro Leu Ser Arg Val Pro Asn Thr
            20                  25                  30 aag cca cca ttc act gtt ggc caa ctc aag aaa gca att cca cca cac       144
Lys Pro Pro Phe Thr Val Gly Gln Leu Lys Lys Ala Ile Pro Pro His
        35                  40                  45 tgc ttt cag cgc tcc ctc ctc act tca ttc tcc tat gtt gtt tat gac       192
Cys Phe Gln Arg Ser Leu Leu Thr Ser Phe Ser Tyr Val Val Tyr Asp
    50                  55                  60 ctt tca ttt gcc ttc att ttc tac att gcc acc acc tac ttc cac ctc       240
Leu Ser Phe Ala Phe Ile Phe Tyr Ile Ala Thr Thr Tyr Phe His Leu
65                  70                  75                  80 ctt cct caa ccc ttt tcc ctc att gca tgg cca atc tat tgg gtt ctc       288
Leu Pro Gln Pro Phe Ser Leu Ile Ala Trp Pro Ile Tyr Trp Val Leu
                85                  90                  95 caa ggt tgc ctt ctc act ggt gtg tgg gtg att gct cac gag tgt ggt       336
Gln Gly Cys Leu Leu Thr Gly Val Trp Val Ile Ala His Glu Cys Gly
            100                 105                 110 cac cat gcc ttc agc aag tac caa tgg gtt gat gat gtt gtg ggt ttg       384
His His Ala Phe Ser Lys Tyr Gln Trp Val Asp Asp Val Val Gly Leu
        115                 120                 125 acc ctt cac tca aca ctt tta gtc cct tat ttc tca tgg aaa ata agc       432
Thr Leu His Ser Thr Leu Leu Val Pro Tyr Phe Ser Trp Lys Ile Ser
```

|   |   |
|---|---|
| cat cgc cgc cat cac tcc aac aca ggt tcc ctt gac cgt gat gaa gtg<br>His Arg Arg His His Ser Asn Thr Gly Ser Leu Asp Arg Asp Glu Val<br>145                        150                      155                  160 | 480 |
| ttt gtc cca aaa cca aaa tcc aaa gtt gca tgg ttt tcc aag tac tta<br>Phe Val Pro Lys Pro Lys Ser Lys Val Ala Trp Phe Ser Lys Tyr Leu<br>                165                      170                      175 | 528 |
| aac aac cct cta gga ggg ctg ttt ctc ttc tcg tca cac tca caa<br>Asn Asn Pro Leu Gly Gly Leu Phe Leu Phe Ser Ser His Ser Gln<br>            180                      185                      190 | 573 |
| tagggtggcc tatgtattta gccttcaatg tctctggtag accctatgat agttttgcaa | 633 |
| gccactacca cccttatgct cccatatatt ctaaccgtga gaggcttctg atctatgtct | 693 |
| ctgatgttgc tttgttttct gtgacttact ctctctaccg tgttgcaacc ctgaaagggt | 753 |
| tggtttggct gctatgtgtt tatggggtgc ctttgctcat tgtgaacggt tttcttgtga | 813 |
| ctatcacata tttgcagcac acacactttg ccttgcctca ttacgattca tcagaatggg | 873 |
| actggctgaa gggagctttg gcaactatgg acagagatta tgggattctg aacaaggtgt | 933 |
| ttcatcacat aactgatact catgtggctc accatctctt ctctacaatg ccacattacc | 993 |
| atgcaatgga ggcaaccaat gcaatcaagc caatattggg tgagtactac caatttgatg | 1053 |
| acacaccatt ttacaaggca ctgtggagag aagcgagaga gtgcctctat gtggagccag | 1113 |
| atgaaggaac atccgagaag ggcgtgtatt ggtacaggaa caagtattga | 1163 |

<210> SEQ ID NO 21
<211> LENGTH: 191
<212> TYPE: PRT
<213> ORGANISM: Glycine max

<400> SEQUENCE: 21

Met Gly Leu Ala Lys Glu Thr Thr Met Gly Gly Arg Gly Arg Val Ala
1               5                   10                 15

Lys Val Glu Val Gln Gly Lys Lys Pro Leu Ser Arg Val Pro Asn Thr
               20                   25                 30

Lys Pro Pro Phe Thr Val Gly Gln Leu Lys Lys Ala Ile Pro Pro His
              35                   40                  45

Cys Phe Gln Arg Ser Leu Leu Thr Ser Phe Ser Tyr Val Val Tyr Asp
50                    55                   60

Leu Ser Phe Ala Phe Ile Phe Tyr Ile Ala Thr Thr Tyr Phe His Leu
65               70                   75                 80

Leu Pro Gln Pro Phe Ser Leu Ile Ala Trp Pro Ile Tyr Trp Val Leu
               85                   90                 95

Gln Gly Cys Leu Leu Thr Gly Val Trp Val Ile Ala His Glu Cys Gly
              100                 105                110

His His Ala Phe Ser Lys Tyr Gln Trp Val Asp Asp Val Val Gly Leu
              115                 120                125

Thr Leu His Ser Thr Leu Leu Val Pro Tyr Phe Ser Trp Lys Ile Ser
           130                      135                    140

His Arg Arg His His Ser Asn Thr Gly Ser Leu Asp Arg Asp Glu Val
145                        150                      155                  160

Phe Val Pro Lys Pro Lys Ser Lys Val Ala Trp Phe Ser Lys Tyr Leu
               165                      170                      175

Asn Asn Pro Leu Gly Gly Leu Phe Leu Phe Ser Ser His Ser Gln
            180                      185                      190

METHOD TO DEVELOP HIGH OLEIC ACID SOYBEANS USING CONVENTIONAL SOYBEAN BREEDING TECHNIQUES

CROSS-REFERENCE TO RELATED APPLICATIONS

This application is a divisional of co-pending U.S. Nonprovisional application Ser. No. 13/351,757, filed Jan. 17, 2012, which claims benefit of priority to U.S. Provisional Application Ser. No. 61/433,120 filed Jan. 14, 2011.

GOVERNMENT RIGHTS STATEMENT

This invention was made with government funding under Grant Number 58-6645-8-121, provided by the United States Department of Agriculture, Agricultural Research Service (USDA/ARS). The government has certain rights in the invention.

SEQUENCE LISTING

This application is accompanied by a sequence listing both on paper and in a computer readable form that accurately reproduces the sequences described herein.

BACKGROUND

Plant oils are used in a variety of applications. Novel vegetable oil compositions and improved approaches to obtain oil compositions, from biosynthetic or natural plant sources, are needed. Depending upon the intended oil use, various different fatty acid compositions are desired. Plants, especially species which synthesize large amounts of oils in seeds, are an important source of oils both for edible and industrial uses.

Oleic acid is a monounsaturated omega-9 fatty acid found in various animal and vegetable sources. It is considered one of the healthier sources of fat in the diet and is commonly used as a replacement for fat sources that are high in saturated fats.

Diets in which fat consumption are high in oleic acid have been shown to reduce overall levels of cholesterol, arteriosclerosis and cardiovascular disease. Specifically, oleic acid has been shown to raise levels of high-density lipoproteins (HDLs) known as "good cholesterol", while lowering low-density lipoproteins (LDLs) also known as the "bad" cholesterol. Thus, the development of new and inexpensive sources of foods comprising healthier forms of fatty acid is desirable.

Plants synthesize fatty acids via a common metabolic pathway known as the fatty acid synthetase (FAS) pathway. Beta-ketoacyl-ACP (acyl carrier protein moiety) synthases are important rate-limiting enzymes in the FAS of plant cells and exist in several versions. Beta-ketoacyl-ACP synthase I catalyzes chain elongation to palmitoyl-ACP (C16:0), whereas Beta-ketoacyl-ACP synthase II catalyzes chain elongation to stearoyl-ACP (C18:0). Beta-ketoacyl-ACP synthase IV is a variant of Beta-ketoacyl-ACP synthase II, and can also catalyze chain elongation to 18:0-ACP. In soybeans, the major products of FAS are 16:0-ACP and 18:0-ACP. The desaturation of 18:0-ACP to form 18:1-ACP is catalyzed by a plastid-localized soluble delta-9 desaturase (also referred to as "stearoyl-ACP desaturase").

The products of the plastidial FAS and delta-9 desaturase, 16:0-ACP, 18:0-ACP, and 18:1-ACP, are hydrolyzed by specific thioesterases (FAT). Plant thioesterases can be classified into two gene families based on sequence homology and substrate preference. The first family, FATA, includes long chain acyl-ACP thioesterases having activity primarily on 18:1-ACP. Enzymes of the second family, FATB, commonly utilize 16:0-ACP (palmitoyl-ACP), 18:0-ACP (stearoyl-ACP), and 18:1-ACP (oleoyl-ACP). Such thioesterases have an important role in determining chain length during de novo fatty acid biosynthesis in plants, and thus these enzymes are useful in the provision of various modifications of fatty acyl compositions, particularly with respect to the relative proportions of various fatty acyl groups that are present in seed storage oils.

The products of the FATA and FATB reactions, the free fatty acids, leave the plastids and are converted to their respective acyl-CoA esters. Acyl-CoAs are substrates for the lipid-biosynthesis pathway (Kennedy Pathway), which is located in the endoplasmic reticulum (ER). This pathway is responsible for membrane lipid formation as well as the biosynthesis of triacylglycerols, which constitute the seed oil. In the ER there are additional membrane-bound desaturases, which can further desaturate 18:1 to polyunsaturated fatty acids.

The soybean genome possesses two seed-specific isoforms of a delta-12 desaturase FAD2, designated FAD2-1A and FAD2-1B, which differ at only 24 amino acid residues. The genes encoding FAD2-1A and FAD2-1B are designated Glyma10g42470 on Linkage Group O and Glyma 20g24530 on Linkage Group I on the soybean genome sequence, respectively (Glyma1.0, Soybean Genome Project, DoE Joint Genome Institute). FAD2-1A and FAD2-1B are found in the ER where they can further desaturate oleic acid to polyunsaturated fatty acids. The delta-12 desaturase catalyzes the insertion of a double bond into oleic acid (18:1), forming linoleic acid (18:2) which results in a consequent reduction of oleic acid levels. A delta-15 desaturase (FAD3) catalyzes the insertion of a double bond into linoleic acid (18:2), forming linolenic acid (18:3).

TABLE 1

Characteristics of the major Fatty Acids

| Carbons:Double Bonds | Name | Saturation |
| --- | --- | --- |
| 16:0 | Palmitic Acid | Saturated |
| 18:0 | Stearic Acid | Saturated |
| 18:1 | Oleic Acid | monounsaturated |
| 18:2 | Linoleic Acid | ω-6 polyunsaturated |
| 18:3 | α-Linolenic Acid | ω-3 polyunsaturated |

The designations (18:2), (18:1), (18:3), etc., refer to the number of carbon atoms in the fatty acid chain and the number of double bonds therein, Table 1. As used herein, the designations sometimes take the place of the corresponding fatty acid common name. For example, oleic acid (18:1) contains 18 carbon atoms and 1 double bond, and is sometimes referred to as simply "18:1".

While previous research has demonstrated the important role of the FAD2-1A gene for increasing oleic acid, no reports have demonstrated a direct effect of the FAD2-1B gene on oleic acid accumulation. Soybean is a commodity crop that provides a major component of the fats and oils in the American diet. Soybean is considered an oilseed, and it typically contains about 20% oleic acid as part of the fatty acid profile in the seed oil.

Soybean oil is used by the food industry in a variety of food products including cooking oils, salad dressings, sandwich spreads, margarine, bread, mayonnaise, non-dairy coffee creamers and snack foods. Soybean oil is also used in industrial markets such as biodiesel and biolube markets.

For many oil applications, low saturated fatty acid levels are desirable. Saturated fatty acids have high melting points which are undesirable in many applications. When used as a feedstock or fuel, saturated fatty acids cause clouding at low temperatures, and confer poor cold flow properties such as pour points and cold filter plugging points to the fuel. Oil products containing low saturated fatty acid levels may be preferred by consumers and the food industry because they are perceived as healthier and/or may be labeled as "low in saturated fat" in accordance with FDA guidelines. In addition, low saturate oils reduce or eliminate the need to winterize the oil for food applications such as salad oils. In biodiesel and lubricant applications, oils with low saturated fatty acid levels confer improved cold flow properties and do not cloud at low temperatures.

Various technologies for generating mid to high oleic acid levels in soybean plants are known. For example, U.S. Patent Publication No. 2007/0214516 discloses a method for obtaining soybean plants that have moderately increased levels of oleic acid. However, this technology requires the genetic modification of soybean plants through the introduction of a transgene by transgenesis.

While transgenic soybean lines have been generated that produce soybean oil containing mid to high levels of oleic acid, non-genetically modified (non-GMO) soybean plant lines that produce seed with mid to high oleic acid content is desirable.

SUMMARY

The presently disclosed instrumentalities overcome the problems outlined above and advance the art by providing a method to create and select conventional non-GMO soybean lines containing greater than around 20% and up to around 85% oleic acid in soybean seed oil with up to a four-fold increase over the levels produced by commodity soybeans. The instrumentalities described herein, demonstrate the ability to efficiently incorporate an enhanced oil quality trait into elite varieties of soybean plants without the expensive testing and evaluation used in traditional soybean breeding.

The presently disclosed instrumentalities demonstrate that mutation in the FAD2-1B gene alone resulted in very minor increases in oleic acid levels. However, combinations of mutations in the FAD2-1A and FAD2-1B genes resulted in dramatic increases in oleic acid level of the seed oil.

In an embodiment, a soybean plant having one or more mutations in the FAD2-1A and FAD2-1B genes, wherein seed from said plant has about 75% to about 85% oleic acid content In an embodiment, a soybean plant expressing a mutated FAD2-1B gene encoded by a polynucleotide having at least 70%, 80%, 90%, 95%, 98%, or 99% identity with the sequence of SEQ ID NO: 1 or SEQ ID NO: 3 and expressing a mutated FAD2-1A gene encoded by a polynucleotide having at least 70%, 80%, 90%, 95%, 98%, or 99% identity with the sequence of SEQ ID NO: 7 or expressing M23 mutant characterized by deletion of a FAD2-1A gene having the sequence as set forth in SEQ ID NO: 5 has seed with a modified fatty acid composition that is about 75% to about 85% oleic acid.

In an embodiment, a method of selecting soybean plants with seed having an oleic acid content of between about 65% to about 85%, said method comprising: crossing a first soybean plant having one or more mutations in a first polynucleotide sequence encoding a FAD2-1A comprising the amino acid sequence as set forth in SEQ ID NO: 10 with a second soybean plant having one or more mutations in a second polynucleotide sequence encoding a FAD2-1B comprising the amino acid sequence as set forth in SEQ ID NO: 12 is described.

In an embodiment, a nucleic acid encoding a mutated form of FAD2-1B comprising: a sequence length of at least 72 nucleotides (24 amino acids) encoding SEQ ID NO: 12 or a fragment thereof wherein the sequence includes at least one mutation selected from the group consisting of: a non-conserved amino acid substitution at amino acid position 137, and b. a non-conserved amino acid substitution at amino acid position 143 is described.

In an embodiment, a soybean plant expressing a mutated FAD2-1B gene encoded by a polynucleotide having at least 70%, 80%, 90%, 95%, 98%, or 99% identity with the sequence of SEQ ID NO: 1 or SEQ ID NO: 3 has seed with a modified fatty acid composition that is about 22% to about 41% oleic acid.

In an embodiment, a soybean plant expressing a mutated FAD2-1B gene that results in a reduced activity of the FAD2-1B has seed with a modified fatty acid composition of oleic acid levels greater than about 20%.

In an embodiment, a transgenic soybean plant expressing a dominant negative form of FAD2-1B has seed with a modified fatty acid composition of oleic acid levels greater than 20% preferably between about 20% to 60% and most preferably between about 60% to 85%.

In one aspect, the nonfunctional mutant FAD2-1A and FAD2-1B alleles may be identified by screening naturally occurring soybean plants that have high oleic acid content. Plants with these mutations may be crossed and subjected to conventional breeder-grower techniques to preserve the high oleic trait while selecting also for other such features as high yield, healthy root structure, and other desired phenotypes, in order to provide a variety that stably reproduces these traits among a large population of plants.

DETAILED DESCRIPTION

Figure 1A:
FIGS. 1A and 1B are weblogo outputs showing amino acid conservation of fatty acid desaturase enzymes.

As used herein, "allele" refers to any of one or more alternative forms of a gene locus, all of which alleles relate to a trait or characteristic. In a diploid cell or organism, the two alleles of a given gene occupy corresponding loci on a pair of homologous chromosomes.

As used herein, "FAD2" refers to a gene or encoded protein capable of catalyzing the insertion of a double bond into a fatty acyl moiety at the twelfth position counted from the carboxyl terminus FAD2 proteins are also referred to as "delta-12 desaturase" or "omega-6 desaturase". The term "FAD2-1A" is used to refer to a FAD2 gene or protein defined as Glyma10g42470.1 in the Glyma1.0 whole genome sequence (http://www.phytozome.net/soybean) that is naturally expressed in a specific manner in seed tissue, and the term "FAD2-1B" is used to refer a FAD2 gene or protein defined as Glyma20g24530.1 in the Glyma1.0 whole genome sequence (http://www.phytozome.net/soybean) that is (a) a different gene from a FAD2-1A gene or protein and (b) is naturally expressed in multiple tissues, including the seed.

As used herein, "gene" refers to a nucleic acid sequence that encompasses a 5' promoter region associated with the expression of the gene product, any intron and exon regions and 3' or 5' untranslated regions associated with the expression of the gene product.

As used herein, "genotype" refers to the genetic constitution of a cell or organism.

As used herein, "mutant" means changed in comparison to a reference. Mutant can apply to different alleles of a single gene that are distinguishable by different nucleotide sequence or to different strains of plants where the mutant strain has at least one characteristic that is different from the reference strain. Mutants may arise, for example, by naturally occurring or transgenic processes. Mutations may be by insertion, deletion or truncation. Nonfunctional mutants are those where the mutation prevents gene expression or results in the expression of a wholly or partially nonfunctional protein.

As used herein, "phenotype" refers to the detectable characteristics of a cell or organism, which characteristics are the manifestation of gene expression As used herein, non-genetically modified (non-GMO) means reasonably capable of occurring in nature. An organism is considered non-GMO if it has not been genetically engineered through the addition of exogenous, or recombinant nucleic acid, such as a transgene, to alter the genetic constitution of the organism.

As used herein, "crossing", as used herein, refers to the mating of two parent plants.

As used herein, "F1" refers to first generation progeny of the cross of two plants.

As used herein, "F2" refers to second generation progeny of the cross of two plants.

As used herein, "F3", as used herein, refers to third generation progeny of the cross of two plants.

As used herein, "F4", as used herein, refers to fourth generation progeny of the cross of two plants.

As used herein, "F5", as used herein, refers to fifth generation progeny of the cross of two plants.

As used herein, "F6", as used herein, refers to sixth generation progeny of the cross of two plants.

As used herein, "F7", as used herein, refers to seventh generation progeny of the cross of two plants.

As used herein, "F8", as used herein, refers to eighth generation progeny of the cross of two plants.

As used herein, a recombinant inbred line (RIL) is produced to form a permanent and stable quantitative trait locus (QTL) mapping resource. In the first step of the development of RILs, two parental inbred lines are crossed (mated) together to form a uniformly heterozygous F1 generation. The F1 are intermated (or selfed) to form an F2 generation; most individuals in the F2 will contain recombinant chromosomes resulting from crossovers between the two purely parental chromosomes present in each F1 plant. The parental alleles are said to be segregating in the F2 generation, since it is a matter of chance just which of the three combinations of parental alleles will occur in a given F2 plant. Numerous individuals from the segregating F2 generation then serve as the founders of corresponding RILs. Each subsequent generation of a given RIL is formed by selfing in the previous generation and with single seed descent. In this manner each RIL, after several generations, will contain two identical copies of each chromosome, with most of them being recombinant. Each individual RIL will contain a different mix of recombinant and parental chromosomes, with a unique set of recombination breakpoint locations across the genome. Taken as a group, the set of RILs form a segregant QTL mapping population which can be stably regenerated year after year via single seed descent.

As used herein genotypic designations are as follows:
  AABB—homozygous wild-type FAD2-1A and homozygous wild-type FAD2-1B;
  aaBB—homozygous mutant FAD2-1A (mFAD2-1A) and homozygous wild-type FAD2-1B;
  AAbb—homozygous wild-type FAD2-1A and homozygous mutant FAD2-1B (mFAD2-1B);
  aabb—homozygous mFAD2-1A and homozygous mFAD2-1B As used herein, the soybean plant lines designated "Jake" and "Williams 82" (W82) are conventional soybean varieties that have wild-type levels of oleic acid and wild-type alleles of FAD2-1A and FAD2-1B.

As used herein a Plant Introduction (PI) or plant introduction line is a soybean line assumed to be inbred for multiple generations so that its progeny stably inherit all of the genes that it contains. Plant introduction lines can be local landraces, cultivars, varieties, field collections of locally adapted lines, selections from any of these lines, or advanced breeding lines that have been inbred and have stabilized genomes. The National Plant Germplasm System maintains a collection of Glycine max lines referred to as Plant Introductions.

As used herein, a maturity group is an agreed-on industry division of groups of varieties based on zones in which they are adapted, primarily according to day length or latitude. They consist of very long day length varieties (Groups 000, 00, 0), and extend to very short day length varieties (Groups VII, VIII, IX, X).

A "fatty acid" is a carboxylic acid that generally has a long unbranched aliphatic carbon chain. The designations (18:2), (18:1), (18:3), etc., refer to the number of carbon atoms in the fatty acid chain and the number of double bonds therein, respectively. For example, oleic acid (18:1) contains 18 carbon atoms and 1 double bond. Exemplary fatty acids include:
  omega-3 fatty acids such as:
    alpha-linolenic acid $(CH_3(CH_2CH=CH)_3(CH_2)_7 COOH)$ omega-6 fatty acids such as:
  linoleic acid $(CH_3(CH_2)_4CH=CHCH_2CH=CH(CH_2)_7COOH)$
omega-9 fatty acids such as:
  oleic acid $(CH_3(CH_2)_7CH=CH(CH_2)_7COOH)$
and saturated fatty acids such as:
  palmitic acid $(CH_3(CH_2)_{14}COOH)$
  stearic acid $(CH_3(CH_2)_8COOH)$.

An isolated nucleic acid, as used herein, means a nucleic acid that is free of at least some of the contaminants associated with the nucleic acid or polypeptides occurring in a natural environment and that has a sequence that can encode for a gene.

An isolated nucleic acid can be further defined as among other things, a fragment or a part of the nucleic acid, such as a short sequence of bases from the nucleic acid of at least a length claimed, or a nucleic acid encoding for a truncated form, a modified form, or an iso form of the protein or polypeptide encoded by the nucleic acid. An isolated nucleic acid may include DNA from which the introns are removed. An isolated nucleic acid may be under the control of an exogenous promoter.

As used herein, a mutation may be one or more nucleotide deletions, substitutions or insertions in a polynucleotide sequence. A mutation may be one or more of a missense, nonsense, frameshift, insertion or deletion.

As used herein, a missense mutation is a point mutation in which a single nucleotide is changed in a gene sequence, resulting in an amino acid change in the corresponding amino acid. A missense mutation may result in reduced activity of the protein encoded by the gene, or may result in a nonfunctional protein.

As used herein, a nonsense mutation is a mutation in a sequence of DNA that results in a premature stop codon, or a nonsense codon in the transcribed mRNA, and may result in a truncated protein product. Nonsense mutations may result in reduced activity of the protein encoded by the gene, or may result in a nonfunctional protein.

As used herein, a frameshift mutation is a genetic mutation in a polynucleotide sequence caused by insertion or deletion of a number of nucleotides that is not evenly divisible by three. Due to the triplet nature of gene expression by codons, the insertion or deletion can disrupt the reading frame, or the grouping of the codons, resulting in a different translated protein product than from the original non mutated gene. Frameshift mutations may result in reduced activity of the protein encoded by the gene, or may result in a nonfunctional protein.

As used herein, a deletion results in the loss of any number of nucleotides e.g. from a single base to an entire gene and surrounding polynucleotide sequences. A deletion mutation may result in reduced activity of the protein encoded by the gene, or may result in a nonfunctional protein.

As used herein, an insertion results in the addition of any number of nucleotides e.g. from a single base to many thousands of bases. An insertion mutation may result in reduced activity of the protein encoded by the gene, or may result in a nonfunctional protein.

As used herein, a loss of function mutation is a mutation that renders a protein incapable of carrying out its biological function.

Mutations in isolated polynucleic acids may be made by techniques known in the art such as, but not limited to, site directed mutagenesis.

Mutations may be induced by X-ray, gamma ray or fast neutron irradiation, and treatment with chemical mutagens such as the alkylating agents ethyl-methanesulfonate (EMS) or N-nitroso-N-methylurea NMU). In addition, natural genetic variation can result from mutations that arise from random DNA polymerase errors that occur during DNA replication of a plant genome. Natural genetic variation in plants may also result from activation of DNA repair mechanisms after exposure to natural sources of ionizing or nonionizing radiation.

Soybean plants can be crossed by either natural or mechanical techniques. Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod. The critical day length for flowering ranges from about 13 h for genotypes adapted to tropical latitudes to 24 h for photoperiod-insensitive genotypes grown at higher latitudes. Soybeans seem to be insensitive to day length for 9 days after emergence. Photoperiods shorter than the critical day length are required for 7 to 26 days to complete flower induction.

Soybean flowers typically are self-pollinated on the day the corolla opens. The stigma is receptive to pollen about 1 day before anthesis and remains receptive for 2 days after anthesis, if the flower petals are not removed. Filaments of nine stamens are fused, and the one nearest the standard is free. The stamens form a ring below the stigma until about 1 day before anthesis, then their filaments begin to elongate rapidly and elevate the anthers around the stigma. The anthers dehisce on the day of anthesis, pollen grains fall on the stigma, and within 10 h the pollen tubes reach the ovary and fertilization is completed. Self-pollination occurs naturally in soybean with no manipulation of the flowers. For the crossing of two soybean plants, it is typically preferable, although not required, to utilize artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a soybean flower include, for example, physical removal of the male parts, use of a genetic factor conferring male sterility, and application of a chemical gametocide to the male parts.

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

The plants of the present invention may be used in whole or in part. Preferred plant parts include reproductive or storage parts. The term "plant parts" as used herein includes, without limitation, seed, endosperm, ovule, pollen, roots, tubers, stems, leaves, stalks, fruit, berries, nuts, bark, pods, seeds and flowers. In an embodiment of the present invention, the plant part is a seed.

In one aspect, an isolated polynucleotide may comprise the nucleotide sequence of the PI 283327 mFAD2-1B (SEQ ID NO: 1) or fragment thereof. Alternatively, a polynucleotide may have substantial sequence similarity to SEQ ID NO: 1, for example, with at least 80%, 90%, 95%, 98%, or 99% sequence identity to the sequence of SEQ ID NO: 1. In another aspect, a polynucleotide may have substantial sequence similarity to the nucleotide sequence of PI 567189A mFAD2-1B (SEQ ID NO: 3), for example, with at least 70%, 80%, 90%, 95%, 98%, or 99% sequence identity to the sequence of SEQ ID NO: 3.

The expression of a protein is generally regulated by a non-coding region of a gene termed a promoter. When a promoter controls the transcription of a gene, it can also be said that the expression of the gene (or the encoded protein) is driven by the promoter. When a promoter is placed in proximity of a coding sequence, such that transcription of the coding sequence is under control of the promoter, it can be said that the coding sequence is operably linked to the promoter. A promoter that is not normally associated with a gene is called a heterologous promoter.

In an embodiment, the expression of the delta-12 desaturase protein encoded by SEQ ID NO: 1, SEQ ID NO: 3 or SEQ ID NO: 7, or the expression of a mutant delta-12 desaturase protein encoded by a polynucleotide sequence characterized by deletion of a FAD2-1A gene having the sequence as set forth in SEQ ID NO: 5, alone or in combination may function as a "dominant negative" protein mutation. Dominant negative or antimorphic mutations occur when the gene product adversely affects the normal, wild-type gene product within the same cell. This usually occurs if the product can still interact with the same elements as the wild-type product, but block some aspect of its function. Such proteins may be competitive inhibitors of the normal protein functions.

The peptides encoded by SEQ ID NO: 1, SEQ ID NO: 3 and SEQ ID NO: 7 of the present disclosure or the peptide encoded by a polynucleotide sequence characterized by deletion of a FAD2-1A gene having the sequence as set forth in SEQ ID NO: 5 of the present disclosure may be prepared by chemical synthesis known to those of skill in the art. The peptides may also be produced using an expression vector having a nucleotide sequence encoding the peptide(s) of choice. The nucleotide sequence may be operably linked to an appropriate promoter, enhancer, terminator, or other sequences capable of regulating the expression of the encoded peptide. The nucleotide sequence may also be operably linked to other functional sequences. In one aspect, such a functional sequence may be a sequence encoding a purification tag, to facilitate expression and purification of the peptides. In another aspect, such a functional sequence may encode an accessory peptide that confers upon the core peptide various properties that are beneficial for the therapeutic functionality of the core peptide, for example, by increasing the stability of the core peptide, or by facilitating the delivery of the core peptide to its therapeutic target tissue or organ in the body.

The terms "protein," "polypeptide," "peptide," and "enzyme" may be used interchangeably in this disclosure, all of which refer to polymers of amino acids. In addition to the peptides explicitly disclosed herein, certain "conservative" substitutions may be made on these peptides without substantially altering the functionality of the peptides.

As generally understood in the art, conserved amino acid residues among orthololgous proteins are the result of evolutionary pressure to maintain biological function and/or folding the protein. An amino acid position conserved among orthologous sets of genes can be involved in many aspects of structure and function. Invariant positions, or those showing conservation of certain residue properties (e.g. charge, hydrophobicity, etc.) are less likely to tolerate mutations than those where the protein family permits mutations to a great variety of amino acids. Positional amino acid sequence conservation based on database sequence deposits, for example, is useful in the determination of amino acid substitutions that may have a deleterious affect on protein folding and/or biological function.

Computer algorithmic sequence alignment programs may be used to predict whether an amino acid substitution affects protein function based on sequence homology and the physical properties of amino acids. Amino acid substitution prediction methods such as, but not limited to, SIFT, PolyPhen, SNPs3D, PANTHER PSEC, PMUT and TopoSNP may be used to predict the effect of an amino acid substitution on protein function. Such prediction methods may be used to determine amino acid substitutions that may result in a loss of function or a reduced activity of the FAD2-1A and/or FAD2-1B genes.

Conservative amino acid substitutions are generally defined as the replacement of one or more amino acids for a different amino acid or amino acids, that preserve the structural and functional properties of proteins.

"Non-conservative" substitutions of one amino acid for another are substitutions of amino acids having dissimilar structural and/or chemical properties, and are generally based on differences in polarity, charge, hydrophobicity, hydrophilicity and/or the amphipathic nature of the residues involved. The substituting amino acids may include naturally occurring amino acids as well as those amino acids that are not normally present in proteins that exist in nature.

The following examples illustrate the present invention. These examples are provided for purposes of illustration only and are not intended to be limiting. The chemicals and other ingredients are presented as typical components or reactants, and various modifications may be derived in view of the foregoing disclosure within the scope of the invention.

Example 1

Isolation and Characterization of High Oleic Acid Content Soybean Plant Lines

About 40 soybean strains with elevated oleic acid content were selected. Three breeding lines, including a patented accession strain M23 (U.S. Pat. No. 7,326,547), were noted as having different genes that affect oleic acid concentration. M23 has an oleic acid content of about 40%-50% of its total fatty acid profile. As described below, fatty acid profiles are represented as a percent of total seed fatty acid content. M23 has a single recessive gene, designated as ol for higher oleic acid content (Takagi, Y. & Rahman, S. M. Inheritance of high oleic acid content in the seed oil) of soybean mutant M23. *Theoretical Applied Genetics* 92, 179-182 (1996)). A recent study revealed that of in M23 is the result of a deletion at the FAD2-1A locus (Sandhu et al., 2007). The other two breeding lines were plant introductions (PI) with elevated oleic acid content based on fatty acid data from the Germplasm Resources Information Network (GRIN). GRIN showed that strains PI 283327 and PI 567189A each contained about 41% and 38% oleic acid content, respectively. However, in the University of Missouri-Delta Center Portageville Mo. field tests across six environments between 2005-2007, strains PI 283327 and PI 567189A averaged about 30% oleic acid where as a check cultivar commonly grown by farmers averaged about 22% oleic acid content. These two PIs were later discovered to have mutations at the FAD2-1B locus which results in the higher seed oleic acid content.

Selection and Crosses

Recombinant inbred line from (RIL) population 1 (F6 RIL of Jake×PI 283327), 2 (F2:6 and F2:7 RIL of M23× PI283327) and 3 (F2:5 and F2:7 RIL of M23×PI 567189 A) were created at the same time. Three crosses were made in summer 2005 at the Delta Research Center at Portageville, Mo. including Jake×PI 283327, M23×PI 283327 and M23× PI 567189A. PI 283327 and PI 567189A are two elevated oleic acid lines with maturity group V and IV, respectively (GRIN USDA), while Jake is a conventional high yielding soybean in group V that contains a typical oleic acid content (Shannon, J. G. et al. Registration of 'Jake' Soybean. *Journal of Plant Registration* 129-30 (2007)). M23 was selected for elevated oleic acid after mutagenesis of the cultivar Bay (Takagi, Y. & Rahman, S. M. Inheritance of high oleic acid content in the seed oil) of soybean mutant M23. *Theoretical Applied Genetics* 92, 179-182 (1996). In 2005 and early 2006, F1 seeds were advanced to the F2 generation in Costa Rica. Each RIL tracing to a single F2 plant except population 1 was also advanced in Costa Rica from 2006 to 2007 for F5 seeds. In 2007, a bulk of five seeds from each RIL in each population was analyzed to obtain fatty acid profile for the Costa Rica location. Population 1 was grown in Portageville, Mo. to produce F7 seeds. Population 2 was grown in Portageville, Mo. to produce F6 seeds, and then soybean RILs with more than 60% oleic acid were advanced to the F7 generation. In population 3, only F5 RILs producing more than 60% oleic acid were selected to generate F7 seeds at Portageville, Mo. in subsequent generations.

In the paragraph immediately above, the nomenclature F2:6 means F2-derived F6, meaning that the last common ancestor of the lines was at F1. The F2 plants started the single seed descent to the F6 generation. A representative sample of population 2 constituting at least 2500 seeds has been placed in a deposit according to terms of the Budapest Treaty for conditional release upon of the seeds the granting of an issued patent. This deposit is designated PTA 11061.

Figure 8:
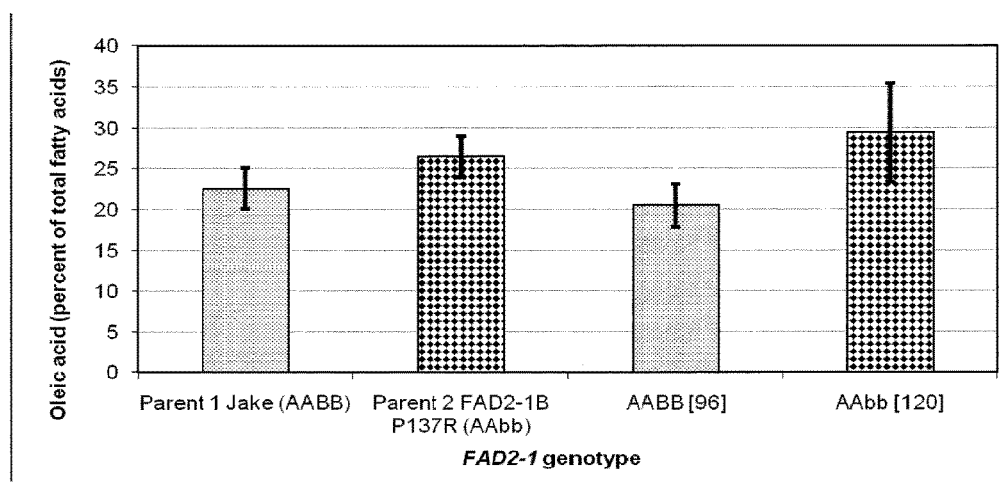
FIG. 8 is a bar graph illustrating oleic acid levels as a function of total fatty acids for population 1.
Figure 9:
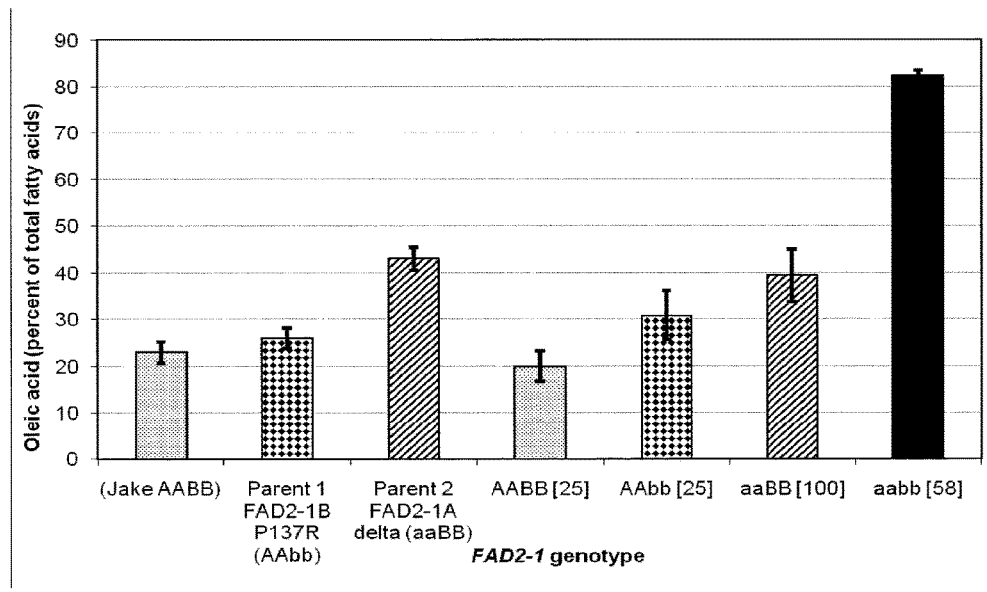
FIG. 9 is a bar graph illustrating oleic acid levels as a function of total fatty acids for population 2.
Figure 10:
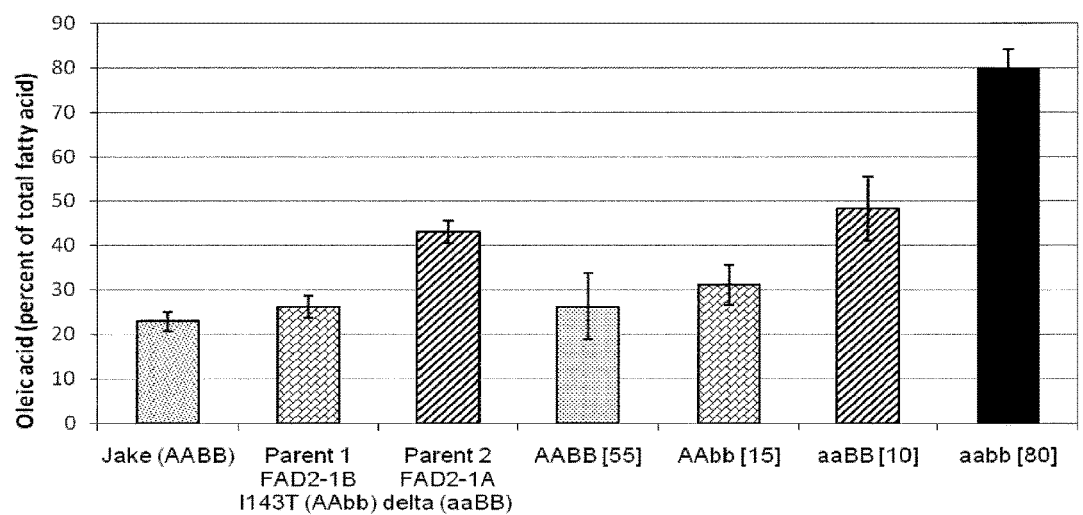
FIG. 10 is a bar graph illustrating oleic acid levels as a function of total fatty acids for population 3.

In 2008, populations 1 and 2 were grown in Portageville, Mo. to produce the seeds analyzed for fatty acids in FIGS. 8 and 9. Data in FIG. 10 was from F5 seeds of population 3 produced in Costa Rica. In addition, five lines with the highest oleic acid content from populations 2 and 3 were grown in Columbia, Mo. in 2009. In 2009, population 4 (17D×(PI 283327×Jake)] was grown in Columbia, Mo. to produce the seeds analyzed for fatty acid analysis in FIG. 5. Similarly, four to eleven lines from each of four combinations of homozygous FAD2-1A and FAD2-1B genes from population 4 were grown in Columbia Mo. and selected lines from population 4 were grown in Portageville, Mo. in 2009.

Population 5 was initiated in summer 2008 at Portageville, Mo. Soybean line KB07-1#123 was crossed with soybean line #93 from population 2. Soybean line #93 (>80% oleic acid) was genotyped to contain the FAD2-1A Δ alleles from M23 and the FAD2-1B P137R alleles derived from PI 283327. KB07-1#123 is a soybean line with the pedigree [W82×(M23×10-73)]. This soybean line was selected to contain three mutant alleles affecting the fatty acid profile, including FAD2-1A Δ alleles from M23, and mutant FAD3A and FAD3C alleles from soybean line 10-73 (Dierking, E. & Bilyeu, K. New sources of soybean seed meal and oil composition traits identified through TILLING. *BMC Plant Biology* 9, 89 (2009); Bilyeu, K., Palavalli, L., Sleper, D. & Beuselinck, P. Mutations in soybean microsomal omega-3 fatty acid desaturase genes reduce linolenic acid concentration in soybean seeds. *Crop Science* 45, 1830-1836 (2005). F1 seeds were genotyped to confirm the heterozygosity and then advanced to obtain F2 seeds in summer 2009 at Bradford Research and Extension Center, Columbia Mo.

Selection for desirable traits may occur at any segregating generation (F2 and above). Selection pressure may be exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

Double mutant, i.e. mFAD2-1A and mFAD2-1B, soybean plant lines may vary in oleic acid concentration depending on the environment, however the oleic acid content (generally up to around 80%-85% oleic acid content) is consistently higher than either wild type or single mFAD1A or mFAD2-1B mutant soybean plant lines.

Crossing of M23 and either PI 283327 or PI 567189A resulted in progeny with levels of oleic acid (around 85% and around 65% respectively) that are significantly higher than either parent (around 20%-50%). This is likely the result of the combination of mutated alleles of FAD2-1A derived from M23, and FAD2-1B derived from PI 283327 or PI 567189A.

When combining a different FAD2-1A gene, from strain 17D (17D has mutant FAD2-1A S117N allele and 35% oleic acid, developed by mutagenesis of Williams 82 seed)×PI 283327, 80% oleic acid lines were also identified. Regardless of the source of the two genes, inheritance of both mutated FAD2-1A and FAD2-1B genes into a single genotype resulted in at least twice the oleic concentration than either parent.

Genetic Characterization of FAD2-1A and FAD2-1B Mutations

For initial characterization of the FAD2-1A and FAD2-1B alleles from multiple germplasm lines, the FAD2-1A and FAD2-1B genes were amplified by PCR and sequenced. Genomic DNA was isolated from approximately 30 mg ground seed using the DNeasy Plant Mini Kit (Qiagen, Inc., Valencia, Calif.). 5 to 50 ng of genomic DNA was used per PCR reaction. PCR was carried out using Ex Taq according to manufacturer's recommendation (Takara, Otsu, Shiga, Japan) in a PTC-200 thermocycler (MJ Research/Bio-Rad, Hercules, Calif.). The forward primer for FAD2-1A was 5'-ACTGCATCGAATAATACAAGCC-3' (SEQ ID NO: 13); and reverse primer was 5'-TGATATTGTCCCGT-GCAGC-3'(SEQ ID NO: 14). The forward primer for FAD2-1B was 5'-CCCGCTGTCCCTTTTAAACT-3'(SEQ ID NO: 15); and reverse primer was 5'-TTACATTATAGCCATG-GATCGCTAC-3'(SEQ ID NO: 16). PCR conditions were: 95° C. for 5 minutes followed by 34 cycles of 95° C. for 30 seconds, 60° C. for 30 seconds, 72° C. for 1 minute 30 seconds. PCR products were examined for size by running on Flashgel for 5 minutes. PCR products were then isolated with the Qiaprep Spin Miniprep kit (Qiagen, Inc.) and sequenced at the University of Missouri DNA core facility using the forward and reverse primers for both FAD2-1A and FAD2-1B. Sequence data was compared with reference "wild-type" Williams 82 sequence (W 82) for the FAD2-1A and FAD2-1B genes. Comparative sequence analysis of all lines tested is illustrated in Table 2.

As illustrated in Table 2, "S>F" represents a serine to phenylalanine amino acid substitution. "M>V" represents a methionine to valine amino acid substitution. "P>R" represents a proline to arginine amino acid substitution. "I>T" represents an isoleucine to threonine amino acid substitution.

PI 283327. PI 578451 was found to contain a FAD2-1B allele identical to PI 567189A. Other germplasm accessions containing variant FAD2-1A and FAD2-1B alleles were also discovered by sequencing.

Figure 1B:
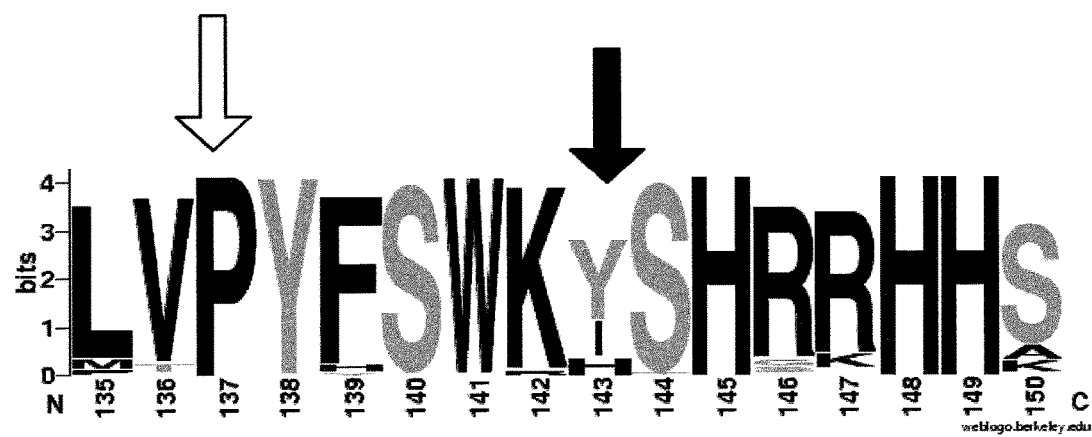

FIG. 1B shows the relative frequency of amino acid substitutions between amino acids 135-150 of the FAD2

TABLE 2

Variants in DNA sequences of FAD2-1B mutants

| | Nucleotide Position | | | | | | | | | |
|---|---|---|---|---|---|---|---|---|---|---|
| | 66 | 105 | 257 (S > F) | 376 (M > V) | 410 (P > R) | 428 (I > T) | 636 | 657/669/682 | 724 (M > L) | 918 |
| Soybean lines | | | | | | | | | | |
| W 82 | G | A | C | A | C | T | C | CTT | T | A |
| PI437593 B | | | | | | | | | | |
| PI467310, PI404160B, PI561338A, PI561315, PI603452 | | | | G | | | | TCC | | G |
| PI567155 B | | | T | G | | | | TCC | | G |
| PI592974, PI196165, PI416908, PI458044 | | G | | G | | | | | | G |
| PI578451, PI567189A | A | | T | G | | C | | TCC | | G |
| PI210179, PI283327 | A | | T | G | G | | | TCC | | G |
| PI567205 | A | | | | | | | | | |
| PI458238 | A | G | | G | | | | | | G |
| PI506885, PI507307 | A | | T | G | | | | TCC | | G |
| PI507420 | A | G | | G | | | | TCC | | G |

DNA sequence analysis revealed that PI 283327 was found to contain a C to G nucleotide substitution at nucleotide 410 in the coding sequence (mRNA) of FAD2-1B resulting in a proline to arginine amino acid substitution missense mutation at amino acid 137 (P137R). In contrast, PI 567189A was found to contain a T to C nucleotide substitution at nucleotide 428 in the coding sequence of FAD2-1B resulting in an isoleucine to threonine missense mutation at amino acid 143 (I143T). Other single nucleotide polymorphisms were present in the allele, but either did not change the amino acid sequence (silent mutations), contained missense mutations substituting similar amino acids (methionine to valine at amino acid position 126 (M126V), for example), or missense mutations in nonconserved regions of the protein (serine to phenylalanine at amino acid position 86 (S86F), for example).

Previously, investigation of the S86F mutation in a different germplasm accession with this mutation, was not associated with an increase in oleic acid content, even in the presence of the FAD2-1A deleted allele from M23. The FAD2-1B P137R mutation is in a very conserved position in the protein, while the I143T mutation is in a less conserved position (FIG. 1B). Subsequent to these discoveries, PI 210179 was found to contain a FAD2-1B allele identical to gene sequences present in the National Center for Biotechnology Information sequence database. A Weblogo output was determined by the amino acid conservation of fatty acid desaturase enzymes aligned as part of the BLINK feature at NCBI using GI number 197111724 Amino acid positions within the protein are listed on the X axis. The overall height for each amino acid column stack indicates the sequence conservation at that position while the height of one-letter amino acid symbols within the column stack indicates the relative frequency of each amino acid in that position [Crooks G E, Hon G, Chandonia J M, Brenner S E WebLogo: A sequence logo generator, Genome Research, 14:1188-1190, (2004)]. The white and black arrows indicate the P137R and I143T positions mutated in PI 283327 and PI 567189A, respectively.

FIG. 1A is reproduced from Dierking and Bilyeu, 2009, BMC Plant Biology 9:89 to show Weblogo output of the relative frequency of amino acid substitutions/amino acid conservation between amino acids 104-123 of the FAD2 gene. Amino acid positions within the protein are listed on the X axis. The overall height for each amino acid column stack indicates the sequence conservation at that position while the height of one-letter amino acid symbols within the column stack indicates the relative frequency of each amino acid in that position. The arrow indicates the FAD2-1A S117N position mutated in line 17D.

Much work has been done with the M23 FAD2-1A gene, but initial results with the 17D line suggest that 80% oleic acid soybean lines can be produced with either source of the FAD2-1A mutation in combination with a FAD2-1B mutation (described below).

The High Oleic Acid Phenotype is Stable in Plants Grown in Alternate Environments Some of the high oleic acid soybean lines developed in this study demonstrated stability for the high oleic acid trait when grown in different environments (Table 3). Of the three environments, Costa Rica typically has the warmest temperatures during seed development, followed by the Portageville, Mo. environment; the Columbia, Mo. environment is the coolest of the three environments during seed development. The differences in the oleic acid contents between environments when the FAD2-1B P137R alleles were present were minor. Soybean lines with genotype aabb of population 2 and 4 produced more than 80% oleic acid content in Costa Rica and Portageville, Mo. environments, and the oleic acid level was an average of 2-4% lower when grown in the Columbia, Mo. environment. It is notable that the variation in the phenotype was narrow in all of the environments. In contrast, the aabb soybean lines of population 3 containing the FAD2-1B I143T alleles had lower and more variable oleic acid content in the cooler environments, and failed to produce a high oleic acid phenotype in either the Columbia, Mo. or Portageville, Mo. environments.

TABLE 3

Oleic acid content and seed generation of soybean lines with different combinations of mutant FAD2-1A and mutant FAD2-1B produced in three environments.

| Population | FAD2-1A | FAD2-1B | Oleic acid content (percent of total fatty acid) | | |
|---|---|---|---|---|---|
| | | | Costa Rica[1] | Portageville, MO[2] | Columbia, MO[3] |
| 2 | Δ | P137R | $81.4 \pm 5.7^{F5}$ | $82.2 \pm 1.2^{F7}$ | $79.1 \pm 1.3^{F8}$ |
| 3 | Δ | I143T | $80.0 \pm 4.0^{F5}$ | $65.0 \pm 4.3^{F7}$ | $58.7 \pm 7.7^{F8}$ |
| 4 | S117N | P137R | $81.1 \pm 2.2^{F2}$ | $81.7 \pm 2.1^{F3}$ | $77.3 \pm 2.0^{F3}$ |

[1]Research station in Costa Rica. Seeds of $F_5$ generation of population of 2 and 3 were produced in winter 2006-2007, while F2 seeds of population 4 were produced in winter 2008-2009.
[2]Plants were grown in Delta Research Center, seeds of F7 generation of the populations 2 and 3 were produced in summer 2008 and F3 generation of population 4 was produced in summer 2009.
[3]All of the plants were grown summer 2009 at the Bradford Research & Extension Center, Columbia MO.

Table 4 illustrates that the high oleic acid phenotype is stable across multiple growing environments, including Portageville, Mo., Columbia, Mo., Stoneville, Miss. and Knoxville, Tenn. Soybean plants inheriting the aabb genotype have oleic acid contents ranging from 72.3-83.2.

TABLE 4

Stability analysis of high oleic acid soybean lines across the environments

| Name | MG | Portageville, MO | | | | | Columbia MO | | | | | Stoneville, MS | | |
|---|---|---|---|---|---|---|---|---|---|---|---|---|---|---|
| | | 16:0 | 18:0 | 18:1 | 18:2 | 18:3 | 16:0 | 18:0 | 18:1 | 18:2 | 18:3 | 16:0 | 18:0 | 18:1 |
| S08-14692 (aabb) | IV | 7.7 | 3.9 | 80.8 | 3.7 | 4.0 | 8.7 | 3.5 | 78.8 | 4.9 | 5.6 | 8.4 | 3.8 | 77.7 |
| S08-14709 (aabb) | IV | 6.6 | 2.9 | 80.1 | 5.0 | 5.4 | 6.8 | 3.0 | 74.3 | 9.0 | 6.9 | 7.3 | 3.2 | 80.9 |
| S08-14705 (aabb) | IV | 6.9 | 2.6 | 83.2 | 3.8 | 3.5 | 6.5 | 3.1 | 80.5 | 4.7 | 5.2 | 7.6 | 3.3 | 78.3 |
| S08-14700 (aabb) | V | 7.5 | 2.4 | 82.1 | 3.7 | 4.3 | 7.5 | 2.9 | 76.5 | 6.9 | 6.2 | 7.9 | 2.7 | 78.9 |
| S08-14702 (aabb) | V | 6.6 | 3.3 | 83.2 | 2.8 | 4.1 | 7.0 | 3.4 | 72.3 | 10.6 | 6.7 | 7.1 | 3.4 | 80.7 |
| S08-14717 (aabb) | V | 7.8 | 2.7 | 81.8 | 3.8 | 4.0 | 7.8 | 3.2 | 76.4 | 6.6 | 5.9 | 8.0 | 2.6 | 80.1 |
| M23 (FAD2-1A parent) (aa) | V | 10.0 | 2.9 | 43.6 | 36.3 | 7.2 | 9.3 | 3.5 | 44.2 | 34.4 | 8.6 | 9.2 | 2.9 | 59.2 |
| PI283327 (FAD2-1B parent) (bb) | V | 10.8 | 4.2 | 27.8 | 46.3 | 10.8 | 10.7 | 4.1 | 23.1 | 49.7 | 12.4 | 11.9 | 3.9 | 30.6 |
| 5002T (Check) (AABB) | IV | 11.2 | 4.3 | 23.8 | 53.1 | 7.6 | 11.2 | 4.2 | 19.8 | 55.1 | 9.6 | 11.3 | 4.5 | 23.9 |
| Anand (Check) (AABB) | V | 12.6 | 3.1 | 19.4 | 55.6 | 9.4 | 12.0 | 3.4 | 18.2 | 55.4 | 11.0 | 12.6 | 3.3 | 20.1 |
| N98-4445A (Check-high oleic) | IV | 8.9 | 3.8 | 55.8 | 29.0 | 2.6 | 9.3 | 4.3 | 46.7 | 36.2 | 3.5 | 9.0 | 3.1 | 63.8 |

| Name | Stoneville, MS | | Knoxville TN | | | | | 18:1 Range | Differences |
|---|---|---|---|---|---|---|---|---|---|
| | 18:2 | 18:3 | 16:0 | 18:0 | 18:1 | 18:2 | 18:3 | | |
| S08-14692 (aabb) | 6.8 | 3.3 | 8.0 | 3.4 | 80.1 | 4.1 | 4.3 | 80.8-77.7 | 3.1 |
| S08-14709 (aabb) | 4.7 | 3.9 | 6.9 | 2.9 | 81.1 | 4.0 | 5.0 | 81.1-74.3 | 6.8 |
| S08-14705 (aabb) | 7.7 | 3.1 | 7.1 | 2.9 | 80.7 | 5.7 | 3.7 | 83.2-78.3 | 4.9 |
| S08-14700 (aabb) | 7.4 | 3.2 | 7.9 | 2.6 | 80.7 | 4.2 | 4.6 | 82.1-76.5 | 5.6 |
| S08-14702 (aabb) | 5.7 | 3.2 | 6.9 | 3.1 | 82.6 | 3.5 | 4.0 | 83.2-72.3 | 10.9 |
| S08-14717 (aabb) | 6.3 | 3.0 | 7.9 | 2.7 | 82.1 | 3.2 | 4.1 | 82.1-76.4 | 5.7 |
| M23 (FAD2-1A parent) (aa) | 23.9 | 4.8 | 9.5 | 2.8 | 52.0 | 29.7 | 6.1 | 59.2-43.6 | 15.6 |
| PI283327 (FAD2-1B parent) (bb) | 46.1 | 7.5 | 11.1 | 4.0 | 25.3 | 48.2 | 11.4 | 30.6-23.1 | 7.5 |
| 5002T (Check) (AABB) | 53.8 | 6.5 | 11.7 | 4.1 | 21.7 | 54.9 | 7.6 | 23.9-19.8 | 4.1 |
| Anand (Check) (AABB) | 55.6 | 8.5 | 12.3 | 3.2 | 21.6 | 54.5 | 8.3 | 21.6-18.2 | 3.4 |
| N98-4445A (Check-high oleic) | 21.9 | 2.2 | 8.8 | 3.5 | 63.6 | 21.8 | 2.3 | 63.8-46.7 | 17.1 |

Lines S08-14692, S08-14709, S08-14705, S08-14700, S08-14702 and S08-14717 are soybean lines selected from a cross of lines M23×PI283327 that inherit the mutant FAD2-1A alleles (aa) from M23 and the FAD2-1B P137R alleles (bb) from PI 283327 and are genotype aabb. Lines Anand and 5002T are soybean lines that are wild-type for the FAD2-1A alleles (AA) and FAD2-1B alleles (BB) and have the genotype AABB. Line N98-4445A a soybean line that contains elevated oleic acid content and carries at least six genes (QTLs) conditioning the high oleic phenotype.

Determination of Fatty Acid Content

Figure 2:
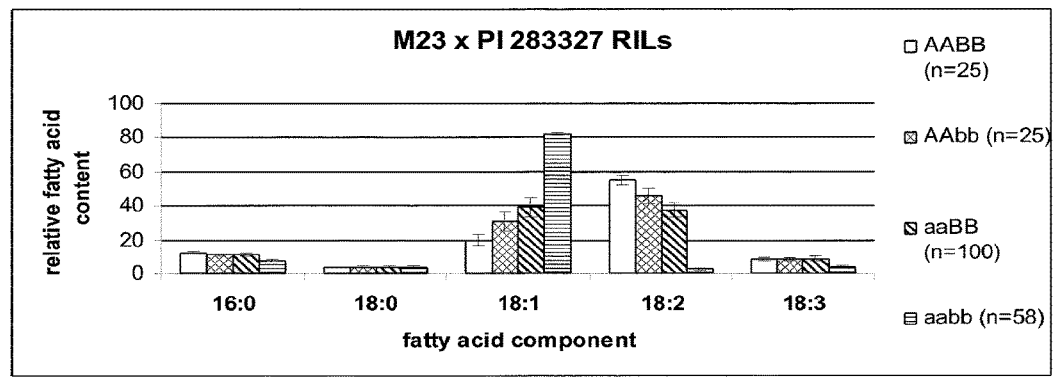
FIG. 2 is a bar graph illustrating the relative fatty acid levels as a function of total fatty acids of progeny from M23×PI 283327 recombinant inbred lines.

Fatty acid profiles as a percent of total oil for each genotype within each environment were determined by Gas Chromatography (GC) as described by Oliva et al. (2006). In most cases, five individual seeds from various strains and crosses were randomly selected for fatty acid analysis. The fatty acid profiles as illustrated in FIG. 2, however, used between either 5 or 10 seeds for measurement. Each five or ten seed sample was placed in a paper envelope, and then manually crushed with a hammer Oil was extracted by placing crushed seeds in 5 mL chloroform:hexane:methanol (8:5:2, v/v/v) overnight. Derivitization was done by transferring 100 µL of extract to vials and adding 75 µL of methylating reagent (0.25 M methanolic sodium methoxide:petroleum ether:ethyl ether, 1:5:2 v/v/v). Hexane was added to bring samples to approximately 1 mL. An Agilent (Palo Alto, Calif.) series 6890 capillary gas chromatograph fitted with a flame ionization detector (275° C.) was used with an AT-Silar capillary column (Alltech Associates, Deerfield, Ill.). Standard fatty acid mixtures (Animal and Vegetable Oil Reference Mixture 6, AOACS) were used as calibration reference standards.

Figure 3:
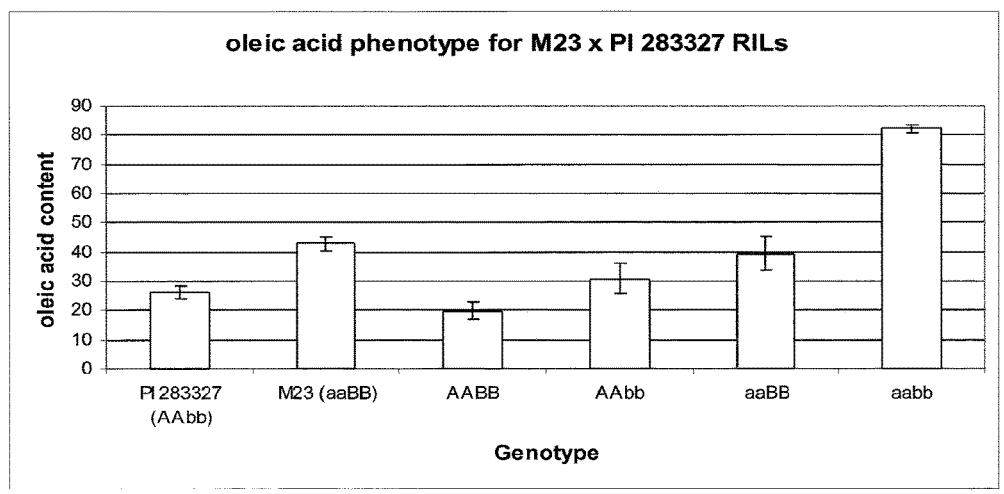
FIG. 3 is a bar graph illustrating the oleic acid content as function of total fatty acids of parents and progeny from M23×PI 283327 recombinant inbred lines.
Figure 4:
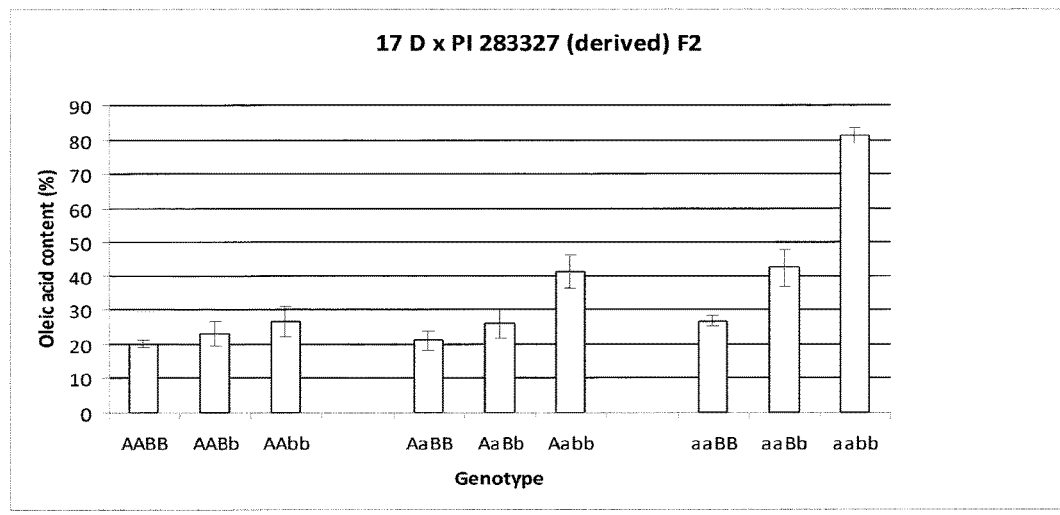
FIG. 4 is a bar graph illustrating the oleic acid content as function of total fatty acids of progeny from 17D×PI 283327 F2 seeds.

As illustrated in FIGS. 2-4, "A" denotes a "wild-type" or non mutated FAD2-1A allele such as carried by reference strain W 82. "a" denotes a mutated FAD2-1A (mFAD2-1A) allele, such as carried by strain M23. "B" denotes a "wild-type" or non-mutated FAD2-1B allele. "b" denotes a mutated FAD2-1B (mFAD2-1B) allele such as carried by strains PI 283327 and PI 567189A. Thus "AA" denotes a homozygous FAD2-1A genotype, "aa" denotes a homozygous mFAD2-1A genotype, "BB" denotes a homozygous FAD2-1B genotype, "bb" denotes a homozygous mFAD2-1B genotype, Aa denotes a heterozygous FAD2-1A/mFAD2-1A genotype and Bb denotes a heterozygous FAD2-1B/mFAD2-1B genotype.

FIG. 2 is a bar graph showing the relative fatty acid content of fatty acid components 16:0, 18:0, 18:1, 18:2 and 18:3 in various allelic variants of F7 progeny derived from M23×PI 283327 recombinant inbred lines (RILs). As can be seen in FIG. 2, progeny homozygous for wild-type FAD2-1A and FAD2-1B (AABB) had oleic acid levels consistent with what is normally found in nature i.e. around 20%. The corresponding byproduct of oleic acid desaturation, linoleic acid levels were around 55%. Mutations in FAD2-1B alone (AAbb) showed only a very minor increase in oleic acid content, ranging from between about 25% to about 30%. Remarkably, progeny with both the mFAD2-1A and mFAD2-1B (aabb) alleles had oleic acid levels around 80%, with the corresponding linoleic acid levels below 5%.

As shown in FIG. 3, oleic acid content was further characterized and compared to the parental lines M23 and PI 283327. Consistent with the results in FIG. 2, seeds with wild-type alleles (AABB) had levels of oleic acid around 20%. Seeds with genotypes of either the aaBB or AAbb had levels of oleic acid around 40% or around 25% respectively. As demonstrated in FIG. 2, while mutations in FAD2-1B alone (AAbb) showed only a very minor increase in oleic acid content, double mutant seeds with the mFAD2-1A and mFAD2-1B (aabb) alleles had oleic acid levels of around 80%. M23 and PI 283327 seeds had oleic acid levels of around 42% and 25%, respectively.

Similar to strain M23, 17D is a strain of soybean that has a mutation in the FAD2-1A gene. As shown in FIG. 4, F2 seeds (produced in Costa Rica in early 2009) homozygous for this mutation showed a small increase in oleic acid levels from around 20% to around 25%. When strain 17D was crossed with a line derived from PI 283327, F2 seeds containing homozygous genes of both mFAD2-1A and mFAD2-1B (aabb) had an oleic acid content of around 80%. FIG. 4 also shows that various heterozygous genotypes had varying levels of oleic acid illustrating that a stratification of oleic acid levels may be obtained through a variation of FAD2-1A and FAD2-1B allele combinations. For example, heterozygous inheritance of 17D mFAD2-1A (Aa) and homozygous inheritance of mFAD2-1B (bb) resulted in seeds with around 45% oleic acid levels.

The initial investigation of both the FAD2-1 genotype and fatty acid phenotype in F2 seeds from Population 4 (FAD2-1A S117N×FAD2-1B P137 cross) demonstrated the epistatic nature of the mutant alleles working in combination, and the results revealed that only homozygous combinations of both mutant FAD2-1A and FAD2-1B were capable of producing the high oleic acid phenotype. Of the 200 F2 seeds that were phenotyped, there were 12 individual F2 seeds with genotype FAD2-1 aabb, and they had an average oleic acid content of 81%, ranging from 75.2% to 83.9% oleic acid (FIG. 4). The next highest oleic acid phenotype in the set was 48.8%, and that seed had the FAD2-1 Aabb genotype. For a two recessive gene model, one sixteenth of the individuals should inherit the phenotype; recovery of 12 individuals with the high oleic acid phenotype satisfies this expectation by Chi-Square test at the 0.05 probability level.

Individuals with a single wild-type version of either FAD2-1A or FAD2-1B in combination with three mutant FAD2-1 alleles (Aabb or aaBb) contained approximately 40% oleic acid. No seeds from any of the other FAD2-1 genotypes contained oleic acid levels above 49% of the seed oil. Individuals with two or more wild-type FAD2-1 alleles contained oleic acid content with a range of 18-47% of the seed oil.

The necessity of the homozygous FAD2-1A and FAD2-1B mutant combination requirement for the high oleic acid phenotype was confirmed in an independent analysis of FAD2-1 genotype and fatty acid phenotype of field produced F2 seeds that contained homozygous FAD2-1A Δ alleles but which were segregating for FAD2-1B P137R alleles (Population 5). While the average oleic acid level of those seeds with the aabb genotype was 82.5%, aaBb seeds averaged 55.4%; aaBB seeds averaged 43.4% oleic acid in the seed oil. The presence of a single wild-type version of the FAD2-1B allele also prevented a high oleic acid content in the seed oil, although the magnitude of the difference was greater for the F2 seeds from Population 4.

Table 5 shows the relative oleic acid content for 14 soybean plant lines derived from M23×PI 283327 between 2006-2007 and 2007-2008. As designated in Table 3, "MT" represents the maturity date in days after August 1, i.e. an MT of 68 indicates that the line matured on October 8. Each of the 14 F6 lines were homozygous recessive for mFAD2-1A and mFAD2-1B. Furthermore, each of the 14 lines traced to a separate F2 plant and are F2:6 recombinant inbred lines. These results derived from seed grown in Costa Rica. Samples from 2006-2007 were of the F5 generation, whereas samples derived from 2007-2008 were of the F6 generation. Oleic acid concentrations were generally near to, or greater than 80%, ranging from around 79% to around 86%.

TABLE 5

Oleic acid content as percentage of total fatty acid for 14 soybean plant lines derived from M23 × PI283327 grown in Costa Rica

| Line | MT 08 | 2006-07 18:1 (F5) | 2007-08 18:1 (F6) |
|---|---|---|---|
| S08-14692 | 56 | 84.5 | 83.8 |
| S08-14693 | 60 | 84.1 | 75.8 |
| S08-14700 | 68 | 84.5 | 84.5 |
| S08-14701 | 68 | 82.0 | 85.5 |
| S08-14702 | 68 | 86.5 | 84.2 |
| S08-14705 | 60 | 81.0 | 84.4 |
| S08-14708 | 58 | 85.4 | 84.6 |
| S08-14709 | 60 | 83.2 | 82.4 |
| S08-14711 | 65 | 83.9 | 82.7 |
| S08-14715 | 68 | 79.6 | 82.2 |
| S08-14716 | 58 | 86.4 | 84.9 |
| S08-14717 | 70 | 86.6 | 85.7 |
| S08-14718 | 65 | 86.4 | 84.4 |
| S08-14719 |  | 85.0 | 83.4 |

Table 6 shows the fatty acid profiles for 14 soybean plant lines derived from M23×PI 283327 performed in 2008. Each of the 14 F6 lines were homozygous recessive for mFAD2-1A and mFAD2-1B. Furthermore, each of the 14 lines traced to a separate F2 plant and is a F2:6 recombinant inbred line. Seed from the 14 soybean lines were grown in Portageville Mo. Oleic acid concentrations were generally near to, or greater than, 80%, and ranged from around 79% to around 85%.

TABLE 6

Fatty acid profiles for 14 F7 soybean plant lines derived from M23 × PI 283327 grown in Portageville Missouri

| Line | 16:0 | 18:0 | 18:1 | 18:2 | 18:3 | Range (18:1) | # of plants |
|---|---|---|---|---|---|---|---|
| S08-14692 | 8.0 | 3.6 | 81.2 | 3.0 | 4.1 | 80.6-81.9 | 15 |
| S08-14693 | 8.5 | 3.2 | 79.3 | 4.6 | 4.5 | 77.7-80.7 | 3 |
| S08-14700 | 8.1 | 3.2 | 82.0 | 2.7 | 4.2 | 80.7-83.9 | 15 |
| S08-14701 | 7.7 | 3.4 | 83.0 | 2.4 | 3.4 | 81.9-84.5 | 15 |
| S08-14702 | 7.0 | 3.8 | 82.9 | 2.4 | 3.9 | 81.5-84.4 | 15 |
| S08-14705 | 8.3 | 3.9 | 82.7 | 1.7 | 3.4 | 81.5-83.9 | 6 |
| S08-14708 | 7.6 | 3.9 | 82.3 | 2.1 | 4.2 | 80.2-83.8 | 9 |
| S08-14709 | 7.6 | 3.5 | 81.3 | 3.0 | 4.6 | 76.4-82.2 | 15 |
| S08-14711 | 8.4 | 4.2 | 80.8 | 2.4 | 4.2 | 79.0-81.6 | 15 |
| S08-14715 | 7.8 | 4.2 | 80.8 | 2.8 | 4.4 | 79.4-82.5 | 15 |
| S08-14716 | 8.8 | 3.2 | 81.3 | 2.8 | 3.8 | 80.3-83.2 | 8 |
| S08-14717 | 8.1 | 3.7 | 82.9 | 1.7 | 3.7 | 81.0-84.0 | 15 |
| S08-14718 | 7.1 | 3.9 | 83.5 | 1.9 | 3.6 | 82.2-84.4 | 15 |
| S08-14719 | 8.7 | 2.8 | 81.6 | 3.5 | 4.0 | 79.3-83.6 | 22 |
| M23 parent | 10.2 | 3.3 | 43.8 | 35.9 | 6.8 | | |
| PI 283327 parent | 11.0 | 4.1 | 26.5 | 47.8 | 10.6 | | |

Table 7 shows the fatty acid profiles from analyses in 2008 for 12 F2 soybean plant lines derived from 17D×S08-14788 (Jake×PI 283327). Oleic acid levels ranged from about 75% to about 84%.

TABLE 7

Fatty acid profiles for 12 F2 soybean lines derived from 17D × S08-14788 (Jake × PI283327)

| Line | 16:0 | 18:0 | 18:1 | 18:2 | 18:3 |
|---|---|---|---|---|---|
| 10 | 7.0 | 2.7 | 83.9 | 2.4 | 4.1 |
| 41 | 8.4 | 3.0 | 75.2 | 7.6 | 5.8 |
| 43 | 7.9 | 3.2 | 81.2 | 2.9 | 4.8 |
| 46 | 7.5 | 2.8 | 83.0 | 2.4 | 4.4 |
| 67 | 7.6 | 3.2 | 81.5 | 2.6 | 5.0 |
| 92 | 7.4 | 3.4 | 81.4 | 2.8 | 4.9 |
| 98 | 7.5 | 3.0 | 82.6 | 2.5 | 4.4 |
| 104 | 8.3 | 3.2 | 81.1 | 2.8 | 4.6 |
| 106 | 7.5 | 2.8 | 80.9 | 3.1 | 5.7 |
| 129 | 7.4 | 3.3 | 82.3 | 2.9 | 4.2 |
| 159 | 8.9 | 3.0 | 79.5 | 2.8 | 5.7 |
| 197 | 7.9 | 3.1 | 80.6 | 3.5 | 4.8 |

Figure 5:
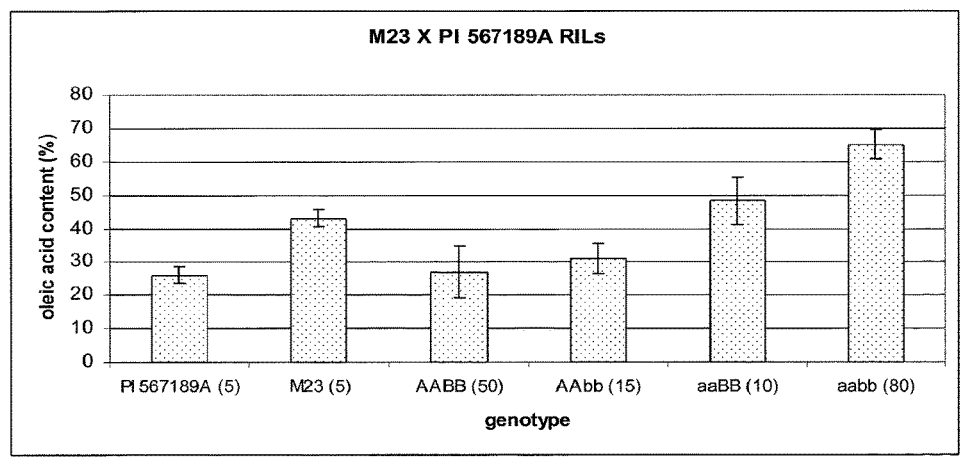
FIG. 5 is a bar graph illustrating oleic acid levels as a function of total fatty acids of progeny from M23×PI 567189A recombinant inbred lines.

Seed (grown in Portageville, Mo. in 2008) derived from a cross between M23 and PI 567189A (M23×PI 567189A) were also analyzed to determine relative amounts of oleic acid. FIG. 5 represents genotype and phenotype analysis for plants that inherited either a wild-type (AA) or deleted version (aa) of the FAD2-1A gene and either a wild-type (BB) or the I143T mutant allele (bb) of FAD2-1B from PI 567189A that differs from the mFAD2-1B allele present in PI 283327 (described above). As shown in FIG. 5, the PI 567189A allele was "weaker" than the PI 283327 allele of mFAD2-1B. Whereas soybean plants inheriting homozygous alleles of both PI 283327 and M23 consistently had levels of oleic acid around 80%, soybean plants inheriting homozygous mutant FAD2-1A and FAD2-1B alleles from PI 567189A and M23 had oleic acid content around 65%.

Figure 6:
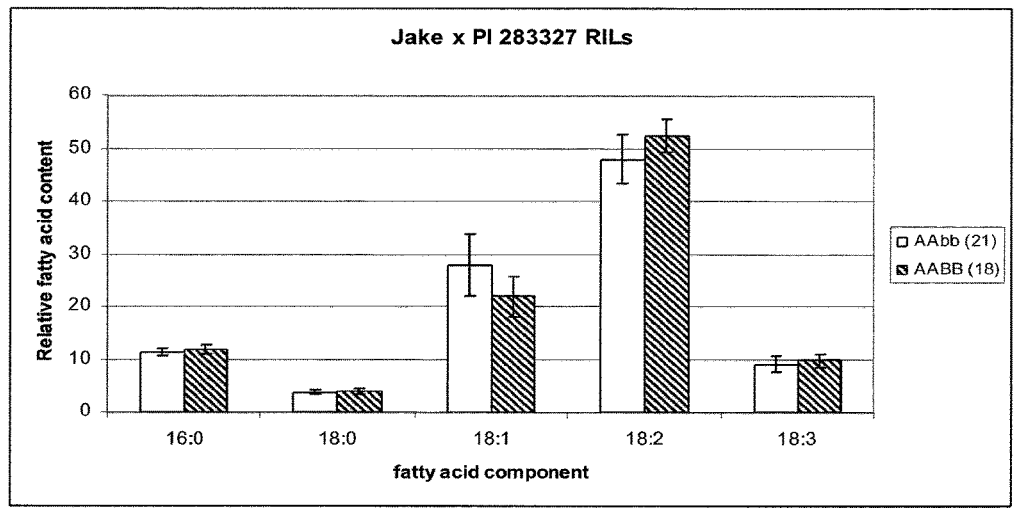
FIG. 6 is a bar graph illustrating oleic acid levels as a function of total fatty acids of progeny from Jake×PI 283327 recombinant inbred lines.

Seed derived from a cross between Jake and PI 283327 (Jake×PI 283327) were also analyzed to determine their fatty acid profile. FIG. 6 represents genotype and phenotype analysis for plants that inherited either a wild-type (AA) version of the FAD2-1A gene and either a wild-type (BB) or the P137R mutant allele (bb) of FAD2-1B from PI 283327 that differs from the mFAD2-1B allele present in PI 567189A (described above). As shown in FIG. 6, the PI 283327 mFAD2-1B allele on the wild-type Jake background (AAbb) had modest effects on oleic acid levels. Whereas, seeds inheriting the AABB genotypes had oleic acid levels of around 20%, seeds inheriting the AAbb genotypes had only a slight increase in oleic acid levels to around 28%.

Taken together these data indicate that plants inheriting loss of function or reduced activity mutations in both the FAD2-1A gene and the FAD2-1B gene produced seed with high levels of oleic acid content ranging from about 75% to about 85%.

The full fatty acid profiles of the seeds of contrasting FAD2-genotypic classes produced from Populations 2, 3, and 4 in this study revealed additional alterations in palmitic acid, linoleic acid, and linolenic acid content (Table 6). As expected for a major decrease in seed expressed FAD2 enzyme activity that results in an accumulation of oleic acid, the FAD2 reaction products linoleic acid and linolenic acid were dramatically reduced in the high oleic FAD2-1A and FAD2-1B homozygous mutant lines when either of the FAD2-1A mutations were present along with the FAD2-1B P137R or I143T alleles.

Table 8. shows fatty acid profiles for different homozygous FAD2-1 genotypes in four segregating populations developed by crossing soybean lines carrying different sources of mutant FAD2-1A alleles with different sources of mutant FAD2-1B alleles.

TABLE 8

Fatty acid profiles of various genotypes.

| | 16:0 | 18:0 | 18:1 | 18:2 | 18:3 |
|---|---|---|---|---|---|
| Population 1 (Jake₁ × PI 283327) | | | | | |
| BB (n = 24) | 12.2 ± 0.9 | 3.9 ± 0.5 | 20.5 ± 2.6 | 53.4 ± 2.8 | 10.0 ± 0.3 |
| bb (n = 30) | 11.2 ± 0.7 | 3.8 ± 0.6 | 29.4 ± 6.0 | 47.0 ± 5.1 | 8.7 ± 0.5 |
| Population 2 (M23 × PI283327) | | | | | |
| AABB (n = 5) | 12.3 ± 0.5 | 3.7 ± 0.4 | 19.9 ± 3.3 | 55.4 ± 2.7 | 8.7 ± 1.0 |
| AAbb (n = 5) | 11.0 ± 0.5 | 3.9 ± 0.4 | 30.8 ± 5.2 | 45.9 ± 4.6 | 8.5 ± 0.9 |
| aaBB (n = 14) | 10.8 ± 0.8 | 3.8 ± 0.6 | 39.4 ± 5.7 | 37.1 ± 4.8 | 8.9 ± 1.2 |
| aabb (n = 16) | 7.9 ± 0.7 | 3.7 ± 0.6 | 82.2 ± 1.2 | 2.3 ± 0.6 | 3.9 ± 0.5 |
| Population 3 (M23 × PI 567189A) | | | | | |
| AABB (n = 11) | 12.5 ± 0.9 | 2.9 ± 0.4 | 26.3 ± 7.4 | 51.4 ± 6.4 | 6.1 ± 1.2 |
| AAbb (n = 3) | 12.4 ± 0.8 | 2.8 ± 0.4 | 31.1 ± 4.5 | 47.5 ± 3.3 | 6.1 ± 1.0 |
| aaBB (n = 1) | 10.3 ± 0.6 | 2.8 ± 0.3 | 48.2 ± 7.2 | 32.5 ± 6.1 | 6.2 ± 0.9 |
| aabb (n = 16) | 8.4 ± 0.8 | 2.6 ± 0.4 | 80.0 ± 4.0 | 5.0 ± 3.0 | 3.8 ± 0.6 |
| Population 4 F2(17D × S08-14788) | | | | | |
| AABB (n = 5) | 12.3 ± 0.9 | 3.2 ± 0.3 | 20.1 ± 0.9 | 55.7 ± 1.0 | 8.7 ± 0.6 |
| AAbb (n = 5) | 12.1 ± 1.0 | 3.4 ± 0.5 | 26.5 ± 4.5 | 47.8 ± 3.7 | 10.2 ± 0.9 |
| aaBB (n = 6) | 11.7 ± 0.3 | 3.0 ± 0.2 | 26.8 ± 1.4 | 48.2 ± 0.7 | 9.9 ± 0.5 |
| aabb (n = 12) | 7.8 ± 0.5 | 3.1 ± 0.2 | 81.1 ± 2.2 | 3.2 ± 1.4 | 4.9 ± 0.6 |
| Population 4 F 2:3 (17D × S0814788) | | | | | |
| AABB (n = 5) | 9.6 ± 0.6 | 3.9 ± 0.4 | 22.4 ± 2.9 | 56.0 ± 2.8 | 8.2 ± 0.9 |
| AAbb (n = 4) | 10.5 ± 0.5 | 3.8 ± 0.3 | 23.1 ± 2.5 | 54.0 ± 2.6 | 8.6 ± 0.5 |
| aaBB (n = 6) | 9.3 ± 0.6 | 3.2 ± 0.3 | 35.0 ± 7.8 | 42.9 ± 5.9 | 9.6 ± 2.2 |
| aabb (n = 11) | 6.9 ± 0.4 | 3.2 ± 0.2 | 77.3 ± 2.0 | 6.3 ± 1.5 | 6.3 ± 0.6 |

*AA = wild-type FAD2-1A alleles, aa = mutant FAD2-1A alleles derived from M23 or 17D, BB = wild-type FAD2-1B alleles, bb = mutant FAD2-1B alleles derived from PI 283327 or PI 567189A.

By evaluating the proportions of oleic, linoleic, and linolenic acids present in the oil extracted from mature seeds, the relative FAD2 and FAD3 desaturase activities of the developing seeds were determined for the contrasting homozygous FAD2-1 genotypes from each population. The FAD2-1 AABB genotypes contained FAD2 desaturase activities (the sum of the final linoleic and linolenic acid contents divided by the sum of final oleic, linoleic, and linolenic acid contents, expressed as a percent) of 76%, 76%, and 74% for Population 2, Population 3, and Population 4, respectively. The FAD2-1 aabb genotypes contained FAD2 desaturase activities of 7%, 10%, and 14%, for Population 2, Population 3, and Population 4, respectively. Also noted is that the accumulation of linolenic acid follows a different pattern for the FAD2-1 aabb mutant lines compared to the FAD2-1 AABB lines, with increased FAD3 desaturase activity (final linolenic acid content divided by the sum of final linoleic and linolenic acid contents) for the FAD2-1 mutant lines.

While no significant differences were observed for the stearic acid levels in the contrasting FAD2-1 genotypes, the aabb mutant lines consistently produced lower palmitic acid levels than lines with the AABB genotype. The most dramatic change was for Population 2. In that case, the content of palmitic acid was 7.9% for the aabb mutant lines compared to 12.3% for the AABB lines.

Because of the concern that improvement in fatty acid profiles might have negative impacts on the total oil and protein profiles of the seeds, we also evaluated the protein and oil contents for the field produced F2:3 seeds from Population 4. There were no significant differences in the protein or oil contents among the different homozygous FAD2 genotypes, or with those lines compared to either Williams 82 or the 17D parental line. The FAD2-1B P137R allele donor parental line had a minor decrease in the average oil content and the highest mean protein content of all of the lines examined.

Genotyping High Oleic Acid Content Soybean Lines PI 283327 and PI 567189A FAD2-1B Alleles from Wild-Type FAD2-1B Alleles Genotyping assays were designed to distinguish the PI 283327 and PI 567189A FAD2-1B alleles from wild-type alleles. The genotyping assays work by asymmetric gene-specific real-time PCR amplification of genomic DNA in the FAD2-1B region surrounding the c410g and t428c single nucleotide polymorphisms (SNPs) in the presence of a fluorescently labeled SimpleProbe (Roche Applied Sciences). After amplification, the PCR products are subjected to a melting curve analysis which tracks the dissociation kinetics of the SimpleProbe from the target DNA. The SimpleProbe has a characteristic melting profile for homozygous wild-type, heterozygous, and homozygous mutant alleles.

The SimpleProbe, GmFAD2-1B, was designed to detect wild-type, heterozygous, and homozygous mutant alleles. GmFAD2-1B SimpleProbe consists of 5'-SPC (simple probe chemistry)-AGTCC$\underline{C}$TTATTTCTCATGGAAAA$\underline{T}$AAGC-Phosphate-3' (SEQ ID NO: 17). The C to G mutation and T to C mutation are indicated by underline. Genotyping reactions were performed with a 5:2 asymmetric mix of primers (5'-ACTGCATCGAATAATACAAGCC-3' (SEQ ID NO: 18); at 2 µM final concentration, and 5'-TGATAT-TGTCCCGTCCAGC-3'(SEQ ID NO: 19); at 5 µM final concentration). Reactions were carried out in 20 µl; containing template, primers, 0.2 µM final concentration of SimpleProbe, and 0.2× Titanium Taq polymerase (BD Biosciences, Palo Alto, Calif.). Genotyping reactions were performed using a Lightcycler 480 II real time PCR instrument (Roche), using the following PCR parameters: 95° C. for 5 minutes followed by 40 cycles of 95° C. for 20 seconds, 60° C. for 20 seconds, 72° C. for 20 seconds, and then a melting curve from 55° C. to 70° C. When DNA from PI 283327 and PI 567189A is amplified with gene specific primers and used in melting curve analysis with the SimpleProbe, a mismatch between the Simpleprobe and the amplicon results in altered disassociation kinetics. Each genotype produced a characteristic melting profile, as measured by Tm of the negative first derivative of the disappearance of fluorescent signal. PI 283327 and all soybean lines with similar FAD2-1B genotype have a characteristic peak of 56.7° C., while PI 567189A yielded a characteristic peak at 60.2° C. M23 and Jake (wild-type for FAD2-1B) have a peak at 62.5° C. Heterozygous individual's genotype showed two peaks at either 56.7° C. or 60.2° C. and 62.5° C.

Figure 7:
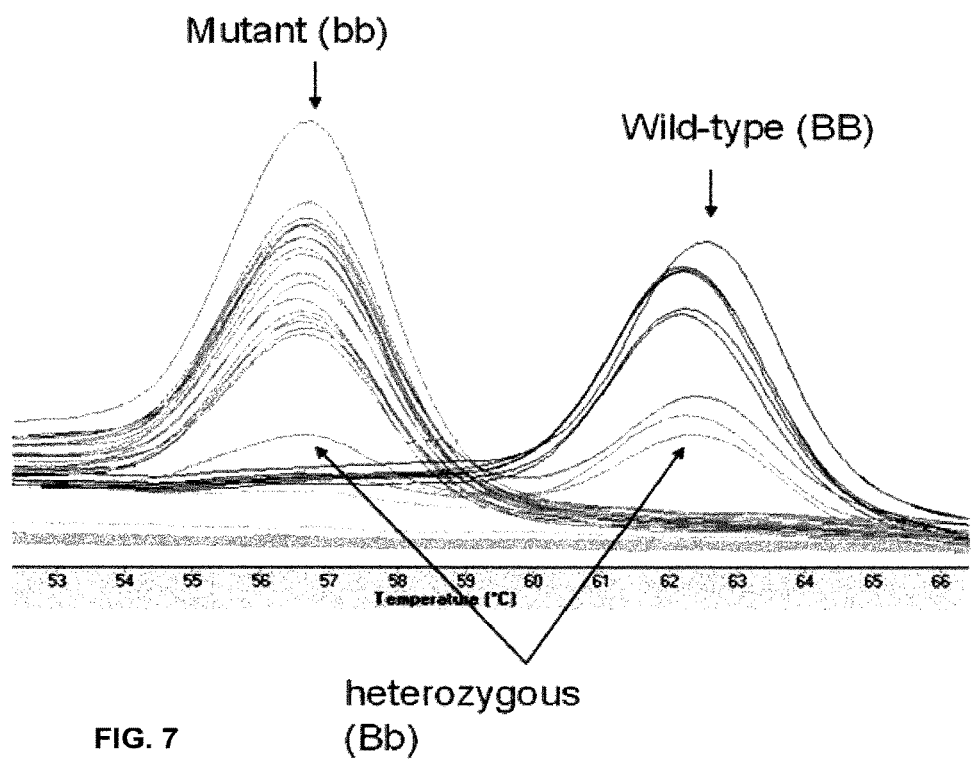
FIG. 7 is a graphical representation of a melting curve analysis used to determine genotype of various FAD2 alleles.

Genotyping for three populations Jake×PI 283327, M23× PI 283327, M23×PI 567189A, were performed with SimpleProbe assay as described. FIG. 7 graphically represents a melting curve analysis with peaks corresponding to homozygous Mutant (bb), wild-type (BB), and Heterozygous (Bb) alleles of FAD2-1B and mFAD2-1B genes.

Effect of Temperature on Oleic Acid Content

Although there is evidence of influence of temperature on the soybean seed oleic acid content, two of our three high oleic acid soybean genotypes proved to be capable of producing a high and stable oleic acid content in three environments. Moreover, there was no reduction in oil and protein content in the evaluated high oleic acid soybean lines. Soybean lines with the combination of FAD2-1A Δ and FAD2-1B I143T alleles from population 3 failed to produce the high oleic phenotype when grown in the nontropical environments. A possible explanation is the mutation in the FAD2-1B allele of PI 567189 A encodes at least nominal enzyme function. This explanation is supported by the fact that the I143T substitution is in a less conserved amino acid of the FAD2 enzyme than the P137R substitution. Other than that, the high oleic acid soybean lines showed a reduction of 4% at most when they were grown in the cooler environment, with a small variation in the oleic acid content. It will be necessary to test the performance of these high oleic acid soybean lines in the main North American soybean growing locations in more northern latitudes. The mutant FAD2-1A and FAD2-1B alleles will have to be combined in soybean lines with the appropriate maturity for those experiments to be conducted. However, based on the stability of the trait that we have observed so far, any reduction of oleic acid content due to the environment is likely to be minor because very little FAD2 enzyme activity remains in developing seeds in the mutant FAD2-1A and FAD2-1B lines. An additional factor is that the end use market has not matured sufficiently to define the exact oleic acid content desired for different oil uses. Another question that should be addressed is whether the trait will affect yield or other agronomic traits. It has been reported that the transgenic soybean lines with the FAD2-1 genes being silenced did not show any yield drag or abnormal physiology characteristics.

The methods and strains, outlined above, function to produce conventional soybean varieties containing an enhanced nutritional oil profile trait high in oleic acid oil. The current yearly demand or oleic acid is approximately four million tons of high oleic acid oil and growing. This figure translates to an annual production of two million acres of high oleic acid soybean to meet the current demand. The availability of soybeans with enhanced oil profile traits may influence the market and increase demand, particularly if the domestic biofuel capacity increases.

As outlined above, transgenic technology is not required, thus eliminating the need for the expensive and time consuming regulatory process. The developed perfect molecular markers and soybean germplasm provide an efficient way to rapidly integrate these desirable traits into additional commercial soybean lines.

Industry has not had access to non-transgenic elite soybean varieties with the high oleic acid trait. The high oleic acid soybean oil is likely to provide a replacement in the food industry for food formulations that previously used partially hydrogenated vegetable oil. Currently, low linolenic acid soybean oil can fulfill some of the demand for alternatives to the trans fat-containing partially hydrogenated vegetable oil. High oleic acid soybean oil adds value by improving functionality of soybean oil in many products such as improving cold flow of biodiesel; better lubricants to withstand high temperature and wider use in foods, pharmaceuticals and other products.

Example 2

Generation of High Oleic Acid Content Soybean Seeds Using Standard Breeder Grower Methods Soybean plant strains are analyzed for mutations that result in loss of function or reduced biological activity of the FAD2-1A or FAD2-1B genes as described above. Soybean plant lines exhibiting impaired activity in either FAD2-1A or FAD2-1B as measured by oleic acid content phenotype, are crossed (mFAD2-1A×mFAD2-1B) to generate progeny that carry both a FAD2-1A mutation a FAD2-1B mutation. These mutations are stably inherited and function synergistically to produce seed with high levels of oleic acid. Fatty acid compositions are analyzed from seed of soybean lines derived from the parental cross using gas chromatography. Seed of the transformed plants exhibit high levels of oleic acid between about 65% to about 85%.

Example 3

Selection of High Oleic Acid Soybean Lines with Additional Desirable Traits

In certain embodiments it may be desirable to select soybeans plants with seeds having high oleic acid content as well as additional desirable traits with various phenotypes of agronomic interest. Examples of additional desirable traits may be, but not limited to, disease resistance, pest resistance, pesticide resistance, accelerated growth rate, high seed yield, ability to grow in diverse environments etc.

A soybean plant with loss of function or reduced activity mutations in FAD2-1A and FAD2-1B is crossed with a soybean plant with one or more desirable traits. Progeny from the cross are analyzed for the presence of the desirable genotypic and phenotypic characteristics deriving from FAD2-1A/FAD2-1B double mutants and the soybean plants with additional desirable traits.

Example 4

Generation of Dominant Negative FAD2 Transgenic Plants

A soybean nucleotide sequence with at least 80%, 90%, 95%, 98%, or 99% sequence identity to the sequence of SEQ ID NO: 1, SEQ ID NO: 3 or SEQ ID NO: 7, or to a sequence encoding M23 mutant characterized by deletion of a FAD2-1A gene having the sequence as set forth in SEQ ID NO: 5 is cloned into an expression vector. The resulting expression constructs are used for transformation of soybean using biolistic methods described below.

The expression vector may have a promoter that functions to express a dominant negative form of mFAD2-1B at levels greater than those seen when expressed with the endogenous or wild-type promoter.

Linear DNA fragments containing the expression constructs for the dominant negative expression of mFAD2-1B desaturase genes are stably introduced into soybean (Asgrow variety A3244 or A4922A32) by the particle bombardment method of McCabe et al. (1988), Bio/Technology, 6:923-926 or via cocultivation with *Agrobacterium tumefaciens*, strain ABI. (Martina, U.S. Pat. No. 6,384,310). Transformed soybean plants are identified by the genotyping assays described above.

Fatty acid compositions are analyzed from seed of soybean lines transformed with the dominant negative expression constructs using gas chromatography.

Example 5

Generation of High Oleic Acid Content Soybean Seeds

Soybean plant seeds are analyzed for spontaneous mutations that result in elevated oleic acid phenotypes, as described above. Soybean plant lines exhibiting impaired activity in either FAD2-1A or FAD2-1B as measured by oleic acid content phenotype, are crossed (i.e. mFAD2-1A× mFAD2-1B) to generate progeny that carry both a FAD2-1A mutation a FAD2-1B mutation. These mutations are stably inherited and function synergistically to produce seed with high levels of oleic acid. Fatty acid compositions are analyzed from seed of soybean lines derived from the parental cross using gas chromatography. Seed of the transformed plants exhibit high levels of oleic acid (over 80%).

Seeds with the dual mutation silencing FAD2-1A and FAD2-1B have been deposited with the American Type Culture Collection in Rockville, Md. as a patent deposit according to the terms and conditions of the Budapest Treaty in a deposit designated PTA-122103.

Strain PI603452 has an alternative FAD2-1A mutation according to (SEQ ID NO: 20) where there is a single base deletion of adenine at position 543/544. This was crossed with P137R allele of FAD2-1B from PI 283327 (SEQ ID NO: 1). Data in Table 9 compares fatty acid profiles of various genotypes under identical growout conditions. The two lines in bold (aabbP1603_744 and aabbP1603_760) represent this new combination of alleles of FAD2-1A from P1 603452 containing a single base deletion and the P137R allele of FAD2-1B from P1 283327. This confirms the mechanism of action by demonstrating that yet another nonfunctional mutant FAD2-1A allele yields more than 80% oleic acid when crossed with a nonfunctional mutant FAD2-1B allele.

TABLE 9

Fatty acid profiles of various genotypes.

|  | 16:0 | 18:0 | 18:1 | 18:2 | 18:3 | 16:0STD | 18:0STD | 18:1STD | 18:2AVG | 18:3AVG |
|---|---|---|---|---|---|---|---|---|---|---|
| aabbP1603 744 | 7.44 | 2.72 | 83.93 | 1.78 | 4.10 | 0.46 | 0.24 | 1.26 | 0.70 | 0.53 |
| aabbP1603 760 | 6.91 | 2.93 | 86.21 | 1.08 | 2.88 | 0.49 | 0.53 | 1.06 | 0.54 | 0.35 |
| aaBB P1603 | 9.43 | 3.21 | 50.83 | 29.17 | 7.35 | 1.05 | 0.30 | 8.53 | 7.33 | 0.86 |
| AAbbP1283327 | 10.31 | 3.28 | 39.02 | 40.49 | 6.88 | 0.82 | 0.37 | 7.45 | 5.28 | 1.82 |
| AABB | 10.31 | 3.28 | 39.02 | 40.49 | 6.88 | 0.82 | 0.37 | 7.45 | 5.28 | 1.82 |
| P1603452 | 11.14 | 3.18 | 31.86 | 46.21 | 7.61 | 0.32 | 0.29 | 5.34 | 5.26 | 1.80 |
| P1283327 | 10.81 | 4.25 | 23.58 | 50.02 | 11.33 | 0.33 | 0.30 | 3.63 | 2.89 | 1.68 |
| W82 | 10.83 | 3.75 | 21.01 | 57.06 | 7.35 | 0.29 | 0.17 | 1.57 | 1.37 | 0.61 |
| Other lines below (2010 data) | | | | | | | | | | |
| M23HO parents (aabb) | 7.3 | 3.5 | 82.7 | 2.3 | 4.2 | 0.2 | 0.3 | 1.7 | 1.1 | 0.8 |
| 17DHO parents (aabb) | 7.3 | 3.4 | 80.2 | 4.1 | 5.0 | 0.3 | 0.4 | 2.0 | 0.9 | 0.7 |

The description of the specific embodiments reveals general concepts that others can modify and/or adapt for various applications or uses that do not depart from the general concepts. Therefore, such adaptations and modifications should are and are intended to be comprehended within the meaning and range of equivalents of the disclosed embodiments. It is to be understood that the phraseology or terminology employed herein is for the purpose of description and not limitation. Certain terms with capital or small letters, in singular or in plural forms, may be used interchangeably in this disclosure.

All references mentioned in this application are incorporated by reference to the same extent as though fully replicated herein.

What is claimed is:

1. A stably reproducing population of soybean seeds comprising a first polynucleotide sequence encoding a mutant FAD2-1A and a second polynucleotide sequence encoding a mutant FAD2-1B, wherein said first polynucleotide sequence comprises a single base deletion of adenine (A) at position 543 or 544 of SEQ ID NO: 9, said FAD2-1A mutant is nonfunctional or has a reduced activity compared to wild-type FAD2-1A; and said second nucleotide sequence is selected from the group consisting of (a) a polynucleotide sequence encoding a FAD2-1B mutant which includes at least one mutation comprising a non-conserved amino acid substitution at amino acid position 137 of SEQ ID NO: 12, and (b) a polynucleotide sequence encoding a FAD2-1B mutant which includes at least one mutation comprising a non-conserved amino acid substitution at amino acid position 143 of SEQ ID NO: 12, said FAD2-1B mutant is nonfunctional or has reduced activity compared to wild-type FAD2-1B, wherein oil from said population of soybean seeds has about 65% to about 85% oleic acid content.

2. The stably reproducing population of soybean seeds of claim 1, wherein said first polynucleotide sequence comprises SEQ ID NO: 20.

3. The stably reproducing population of soybean seeds of claim 1, wherein said second polynucleotide sequence encodes a nonfunctional FAD2-1B mutant or a FAD2-1B mutant having a reduced activity compared to wild-type FAD2-1B which includes at least one mutation comprising a polar amino acid at position 137 of SEQ ID NO: 12.

4. The stably reproducing population of soybean seeds of claim 3, wherein said polar amino acid is selected from the group consisting of arginine, glycine, serine, threonine, cysteine, asparagine, tyrosine, glutamine, lysine and histidine.

5. The stably reproducing population of soybean seeds of claim 1, wherein said second polynucleotide sequence encodes a nonfunctional FAD2-1B mutant or a FAD2-1B mutant having a reduced activity compared to wild-type FAD2-1B which includes at least one mutation comprising a polar amino acid at position 143 of SEQ ID NO: 12.

6. The stably reproducing population of soybean seeds of claim 5, wherein said polar amino acid is selected from the group consisting of arginine, glycine, serine, threonine, cysteine, asparagine, tyrosine, glutamine, lysine and histidine.

7. The stably reproducing population of soybean seeds of claim 1, wherein said first polynucleotide sequence comprises SEQ ID NO: 20, and wherein said second polynucleotide sequence encodes a nonfunctional FAD2-1B mutant or a FAD2-1B mutant having a reduced activity compared to wild-type FAD2-1B which includes at least one mutation comprising a polar amino acid at position 137 of SEQ ID NO: 12.

8. The stably reproducing population of soybean seeds of claim 7, wherein said polar amino acid is selected from the group consisting of arginine, glycine, serine, threonine, cysteine, asparagine, tyrosine, glutamine, lysine and histidine.

9. The stably reproducing population of soybean seeds of claim 1, wherein said first polynucleotide sequence comprises SEQ ID NO: 20, and wherein said second polynucleotide sequence encodes a nonfunctional FAD2-1B mutant or a FAD2-1B mutant having a reduced activity compared to wild-type FAD2-1B which includes at least one mutation comprising a polar amino acid at position 143 of SEQ ID NO: 12.

10. The stably reproducing population of soybean seeds of claim 9, wherein said polar amino acid is selected from the group consisting of arginine, glycine, serine, threonine, cysteine, asparagine, tyrosine, glutamine, lysine and histidine.

11. A soybean plant grown from a soybean seed of the population according to claim 1.

12. A method of producing a soybean plant with seed having a higher oleic acid content compared to a wild-type soybean plant, said method comprising:

(1) crossing the soybean plant of claim 11 with another soybean plant to produce progeny; and (2) preserving about 65% to about 85% oleic acid as a trait in progeny determined by breeder selection to comprise said first and second polynucleotide sequences, thereby producing a soybean plant with seed having a higher oleic acid content compared to a wild-type plant.

13. A method of producing a soybean plant with seed having an oleic acid content of between about 65% to about 85%, said method comprising:

(1) crossing a first soybean plant comprising a first polynucleotide sequence encoding a FAD2-1A mutant, said polynucleotide sequence comprising a single base deletion of adenine (A) at position 543 or 544 of SEQ ID NO: 9, wherein said FAD2-1A mutant is nonfunctional or has a reduced activity compared to wild-type FAD2-1A, with a second soybean plant comprising a second nucleotide sequence selected from the group consisting of (a) a polynucleotide sequence encoding a FAD2-1B mutant which includes at least one mutation comprising a non-conserved amino acid substitution at amino acid position 137 of SEQ ID NO: 12, and (b) a polynucleotide sequence encoding a FAD2-1B mutant which includes at least one mutation comprising a non-conserved amino acid substitution at amino acid position 143 of SEQ ID NO: 12, wherein said FAD2-1B mutant is nonfunctional or has reduced activity compared to wild-type FAD2-1B; and (2) selecting for a progeny soybean plant that comprises said first and second polynucleotide sequences, thereby producing a soybean plant with seed having an oleic acid content of between about 65% to about 85%.

14. The method of claim 13, wherein said first polynucleotide sequence comprises SEQ ID NO: 20.

15. The method of claim 13, wherein said second polynucleotide sequence encodes a nonfunctional FAD2-1B mutant or a FAD2-1B mutant having a reduced activity compared to wild-type FAD2-1B which includes at least one mutation comprising a polar amino acid at position 137 of SEQ ID NO: 12.

16. The method of claim 15, wherein said polar amino acid is selected from the group consisting of arginine, glycine, serine, threonine, cysteine, asparagine, tyrosine, glutamine, lysine and histidine.

17. The method of claim 13, wherein said second polynucleotide sequence encodes a nonfunctional FAD2-1B mutant or a FAD2-1B mutant having a reduced activity compared to wild-type FAD2-1B which includes at least one mutation comprising a polar amino acid at position 143 of SEQ ID NO: 12.

18. The method of claim 17, wherein said polar amino acid is selected from the group consisting of arginine, glycine, serine, threonine, cysteine, asparagine, tyrosine, glutamine, lysine and histidine.

19. The method of claim 13, wherein said first polynucleotide sequence comprises SEQ ID NO: 20, and wherein said second polynucleotide sequence encodes a nonfunctional FAD2-1B mutant or a FAD2-1B mutant having a reduced activity compared to wild-type FAD2-1B which includes at least one mutation comprising a polar amino acid at position 137 of SEQ ID NO: 12.

20. The method of claim 19, wherein said polar amino acid is selected from the group consisting of arginine, glycine, serine, threonine, cysteine, asparagine, tyrosine, glutamine, lysine and histidine.

21. The method of claim 13, wherein said first polynucleotide sequence comprises SEQ ID NO: 20, and wherein said second polynucleotide sequence encodes a nonfunctional FAD2-1B mutant or a FAD2-1B mutant having a reduced activity compared to wild-type FAD2-1B which includes at least one mutation comprising a polar amino acid at position 143 of SEQ ID NO: 12.

22. The method of claim 21, wherein said polar amino acid is selected from the group consisting of arginine, glycine, serine, threonine, cysteine, asparagine, tyrosine, glutamine, lysine and histidine.

* * * * *